United States Patent [19]
Panescu et al.

[11] Patent Number: 6,049,732
[45] Date of Patent: Apr. 11, 2000

[54] ELECTROPHYSIOLOGICAL INTERFACE SYSTEM FOR USE WITH MULTIPLE ELECTRODE CATHETERS

[75] Inventors: Dorin Panescu; David McGee, both of Sunnyvale; Daniel A. Dupree, Saratoga; David F. Dueiri, Santa Clara; David K. Swanson, Mountain View; James G. Whayne, Saratoga; Robert R. Burnside, Mountain View; Tuan Nguyen, San Jose; William Reining, Cross Plains; David W. Arnett, Half Moon Bay, all of Calif.

[73] Assignee: EP Technologies, Inc., San Jose, Calif.

[21] Appl. No.: 08/971,909

[22] Filed: Nov. 17, 1997

[51] Int. Cl.[7] .................................................... A61B 5/00
[52] U.S. Cl. ........................................ 600/523; 600/427
[58] Field of Search .......................... 600/523, 373–375, 600/381, 427, 436, 476, 479; 607/122; 606/41

[56] References Cited

U.S. PATENT DOCUMENTS

| | | | |
|---|---|---|---|
| 5,433,198 | 7/1995 | Desai | 600/373 |
| 5,443,489 | 8/1995 | Ben-Haim | 607/115 |
| 5,509,419 | 4/1996 | Edwards et al. | 600/373 |
| 5,549,108 | 8/1996 | Edwards et al. | 600/373 |
| 5,657,755 | 8/1997 | Desai | 600/373 |

*Primary Examiner*—Jeffrey R. Jastrzab
*Attorney, Agent, or Firm*—Lyon & Lyon LLP

[57] ABSTRACT

A system is used in association with a structure which, in use, is deployed in an interior body region. The structure includes an operative element. A switch matrix is coupled to the operative element. The switch matrix includes a plurality of inputs and a plurality of outputs. A controller is coupled to the switch matrix to control the switch matrix to couple the operative element to selected ones of the inputs and selected ones of the outputs in accordance with applied commands. An interface is coupled to the controller. The interface includes an input element to receive operator input and a processor to generate applied commands to the controller in response to operator input. The interface also includes an image controller to generate an image of the structure while coupled to the switch matrix. The image controller generates markers on the image in response to signals transmitted from the operative element through the switch matrix.

17 Claims, 21 Drawing Sheets

| COMMAND | D0 | D1 | D2 | D3 | D4 | D5 | D6 | D7 |
|---|---|---|---|---|---|---|---|---|
| RESET ALL TO USER DEFINED DEFAULTS | 1 | 0 | 0 | 0 | 0 | 0 | 0 | 0 |
| EXHAUSTIVE O/S TEST | 0 | 1 | 0 | 0 | 0 | 0 | 0 | 0 |
| BY-INPUT O/S TEST | 0 | 0 | 1 | 0 | 0 | 0 | 0 | 0 |
| ENABLE COUNT UP | 0 | 0 | 0 | 1 | 0 | 0 | 0 | 0 |
| ENABLE COUNT DOWN | 0 | 0 | 0 | 0 | 1 | 0 | 0 | 0 |
| DISABLE COUNT | 0 | 0 | 0 | 0 | 0 | 1 | 0 | 0 |
| SET SWITCH ON | 0 | 0 | 0 | 0 | 0 | 0 | 1 | 0 |
| SET SWITCH OFF | 0 | 0 | 0 | 0 | 0 | 0 | 0 | 1 |

FIG. 14

| D7 | D6 | D5 | D4 | D3-0 |
|---|---|---|---|---|
| 0 | 0 | 0 | 0 | 0 |
| 1 | 0 | 0 | 0 | 1 |
| 0 | 0 | 0 | 0 | 2 |
| 1 | 0 | 0 | 0 | 3 |
| 0 | 0 | 0 | 0 | 4 |
| 1 | 0 | 0 | 0 | 5 |
| 0 | 0 | 0 | 0 | 6 |
| 1 | 0 | 0 | 0 | 7 |

FIG. 15

STATUS WORD

| D0 | D1 | D2 | D3 | D4 | D5 | D6 | D7 |
|---|---|---|---|---|---|---|---|
| SWITCH ON/OFF | SHORT | OPEN | COUNT COMPLETED | COUNT ENABLED | COUNT UP/DOWN | COUNT CHANGE | TEST |

FIG. 16

Early Activation Map
17:35:15—Tachycardia ablation site between C6 and C7.

6,049,732

ELECTROPHYSIOLOGICAL INTERFACE SYSTEM FOR USE WITH MULTIPLE ELECTRODE CATHETERS

BACKGROUND OF THE INVENTION

This invention relates generally to systems for diagnosing and treating medical conditions using multiple electrode catheters and, more particularly, to systems and methods of interfacing both personnel and equipment with such catheters.

Multiple electrode catheters are widely used in diagnosing and treating a variety of medical conditions. Today, physicians use such catheters to examine the propagation of electrical impulses in heart tissue to locate aberrant conductive pathways. The techniques used to analyze these pathways, commonly called "mapping," identify regions in the heart tissue, called foci, which can be ablated to treat the arrhythmia.

One form of conventional cardiac tissue mapping technique uses a multiple electrode catheter positioned in contact with epicardial heart tissue to obtain multiple electrograms. The physician stimulates myocardial tissue by introducing pacing signals and visually observes the morphologies of the electrograms recorded during pacing. The physician visually compares the patterns of paced electrograms to those previously recorded during an arrhythmia episode to locate tissue regions appropriate for ablation. These conventional mapping techniques require invasive open heart surgical techniques to position the electrodes on the epicardial surface of the heart.

Another form of conventional cardiac tissue mapping technique, called pace mapping, uses a roving electrode in a heart chamber for pacing the heart at various endocardial locations. In searching for the VT foci, the physician must visually compare all paced electrocardiograms (recorded by twelve lead body surface electrocardiograms (ECG's)) to those previously recorded during an induced VT. The physician must constantly relocate the roving electrode to a new location to systematically map the endocardium.

In still another form of mapping called "impedance mapping," the resistivity of cardiac tissue is measured using an injected current. Infarcted cardiac tissue is detected by virtue of the lower electrical resistivity such tissue displays relative to healthy or normal tissue.

Multiple electrode catheters greatly increase the effectiveness of these various procedures. Such catheters make it possible to simultaneously obtain data from several locations within the heart or other organ using a single catheter. However, as the catheters become more sophisticated, it becomes more and more difficult to process and interpret the resulting data in a meaningful way. Known cardiac mapping and pacing catheters contain as many as sixty-four individual electrodes, each of which can be used for both mapping and pacing. It is reasonable to believe that further advances will enable still more electrodes to be used. Along with the flexibility, resolution and utility provided by such catheters comes the need to process and interpret the resulting data in an efficient, organized manner.

Various approaches have heretofore been taken in processing and interpreting data acquired through multiple electrode catheters. In one prior approach, the various waveforms acquired by the individual electrodes were displayed on a screen. The medical personnel mentally integrated the heart activity and position data as displayed on the recorder and fluoroscopy screens in order to assess the health of the underlying tissue. This approach required a considerable degree of skill and experience on the part of the attending medical personnel. Furthermore, information regarding the relative location of an ablation catheter with respect to the multiple electrodes was not readily available. More significantly, the system became impractical and unwieldy as the number of electrodes increased.

In another prior approach, information acquired from a number of sequential locations of a roving electrode was digitally sampled and combined to construct a model "surface" that was displayed on a screen and that visually represented the tissue under consideration. Although much easier to interpret than the prior approach that required mental integration of various inputs, this system, too, provided an unrealistic representation that required skill and experience to use effectively. Furthermore, the surface was difficult to generate as it required that a roving electrode be moved over the surface of the heart to reconstruct its geometry point by point. To get reasonable accuracy, a high, sometimes impractical, number of points was necessary.

Various other data acquisition systems have been developed for processing data acquired during cardiac mapping and pacing procedures. Typically, such systems record data through multiple recording inputs and process the data to assist the physician in making a diagnosis and rendering treatment. Some systems also include circuitry for generating pacing pulses that can be applied to the heart. Although effective in their intended application, known data acquisition systems become limited in their capabilities as more and more data are provided by more and more sophisticated catheters. Nor do existing systems automatically and continuously monitor the electrodes to warn the physician in the event of a malfunction in the catheter. As catheters become more sophisticated, the number of possible failure modes unavoidably increases. In a multiple electrode system, it is possible for some of the electrodes to be open or shorted.

Many known data acquisition systems only support input from up to twenty-four electrodes and are not directly useful with catheters containing more than twenty-four electrodes. Because data acquisition systems are larger, more complicated and more expensive than the cardiac catheters used in mapping and pacing, it is impractical to redesign a data acquisition system each time an advance is made in the catheter art. Nor is it economically sound for health care providers to retire still serviceable existing systems in favor of the latest model each time a new catheter is introduced. As advances are made in the catheter art, a need develops for adapting the new catheter to use with existing data acquisition systems.

To be of maximum benefit to medical personnel, it is desirable to display information in such a way that it can be easily related by the physician to information provided by existing visualization or imaging systems, such as a fluoroscopic system. Visually based systems, which enable such personnel to "see" what is happening, offer a viable means of presenting large amounts of data in a form that can be readily grasped and understood. Graphical user interfaces are one means by which such a goal can be achieved.

SUMMARY OF THE INVENTION

It is an object of the invention to provide a new and improved apparatus for facilitating the interpretation of data acquired through the use of multiple electrode catheters.

It is a further object of the invention to provide a graphic user interface that facilitates such interpretation.

It is a further object of the invention to provide a graphical user interface that enables medical personnel to visualize a multiple electrode catheter in place within a body.

It is a further object of the invention to provide a graphical user interface that can display the location of roving electrodes with respect to the multiple electrode catheter.

It is a further object of the invention to provide a graphical user interface that can be readily implemented on existing computer apparatus.

One aspect of the invention provides a system comprising a structure which, in use, is deployed in an interior body region. The structure includes an operative element. A switch matrix is coupled to the operative element. The switch matrix includes a plurality of inputs and a plurality of outputs. A controller is coupled to the switch matrix to control the switch matrix to couple the operative element to selected ones of the inputs and selected ones of the outputs in accordance with applied commands. An interface is coupled to the controller. The interface includes an input element to receive operator input and a processor to generate applied commands to the controller in response to operator input. The interface also includes an image controller to generate an image of the structure while coupled to the switch matrix.

In a preferred embodiment, the image controller generates markers on the image in response to signals transmitted from the operative element through the switch matrix.

Another aspect of the invention provides a system comprising a structure which, in use, is deployed in an interior body region. The structure includes an operative element. The system further includes an application specific integrated circuit (ASIC) coupled to the operative element. The ASIC comprises a plurality of inputs, a plurality of outputs, a cross point switch matrix including switching elements realized in a 40–100 volt BiCMOS process coupled to the inputs and to the outputs. The ASIC further includes a control circuit coupled to the cross point switch matrix for controlling the cross point switch matrix to couple selected ones of the inputs with selected ones of the outputs in accordance with applied commands. The system includes an interface coupled to the control circuit. The interface includes an input element to receive operator input and a processor to generate applied commands to the control circuit in response to operator input. The interface further includes an image controller to generate an image of the structure while coupled to the ASIC.

In a preferred embodiment, the image controller generates markers on the image in response to signals transmitted from the operative element through the ASIC.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, wherein like reference numerals identify like elements, and wherein:

FIG. 4 is a simplified block diagram of the interface unit shown in FIGS. 1–3 useful in understanding the operation thereof.

FIG. 14 is a table showing one preferred format for command words used to control the function and operation of the ASIC.

FIG. 15 is a table showing an alternative format wherein parity checking is provided.

FIG. 16 is a table showing one preferred format for a status word used to reflect the current operational status of the ASIC during ASIC operation.

DESCRIPTION OF THE PREFERRED EMBODIMENT

The Diagnostic/Therapeutic System

Figure 1:
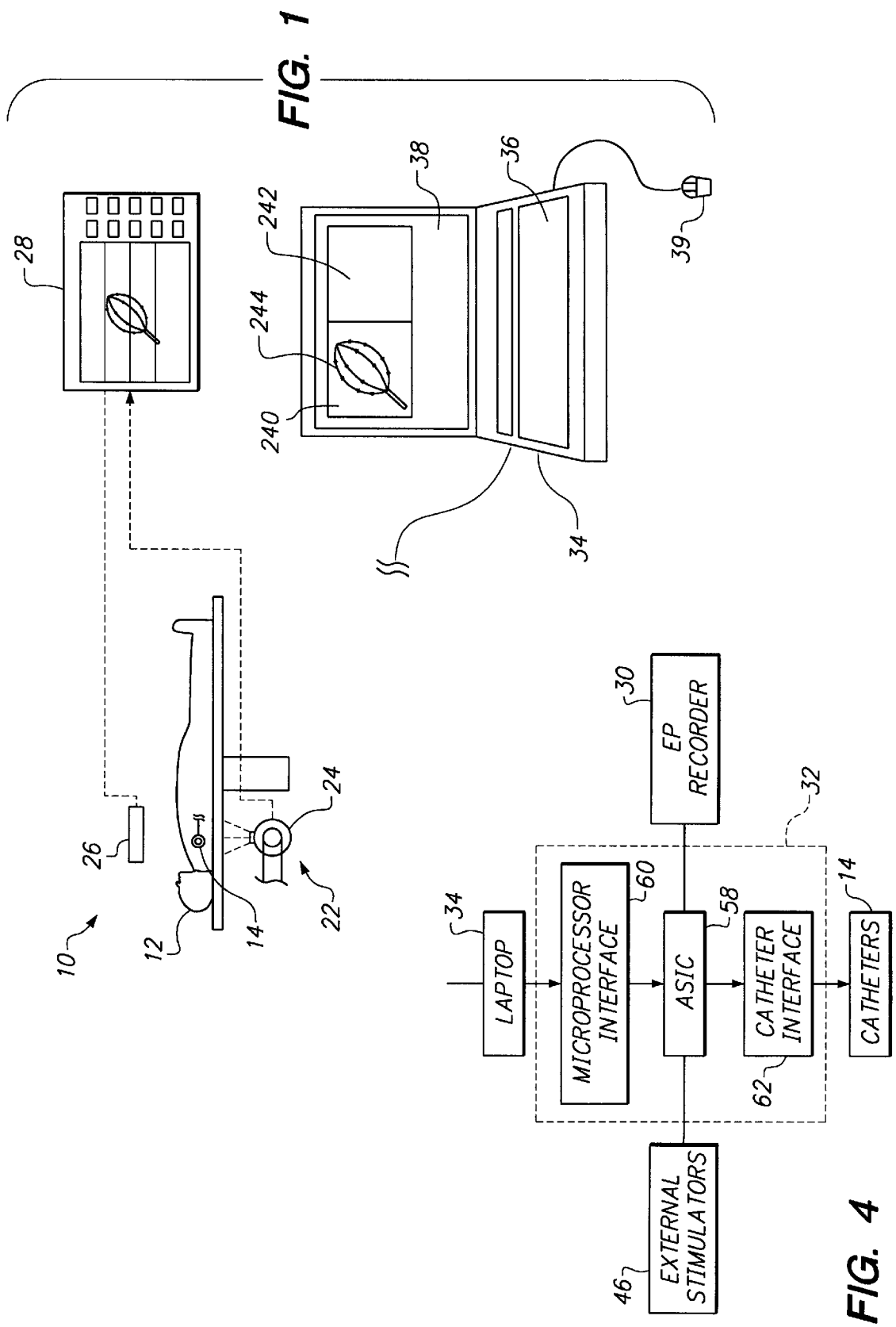
FIG. 1 is a simplified block diagram of a cardiac diagnostic and treatment system having a multiple electrode catheter, an interface unit, a fluoroscope for monitoring the position of the multiple electrode catheter within a patient's body, and a GUI embodying various features of the invention.
Figure 2:
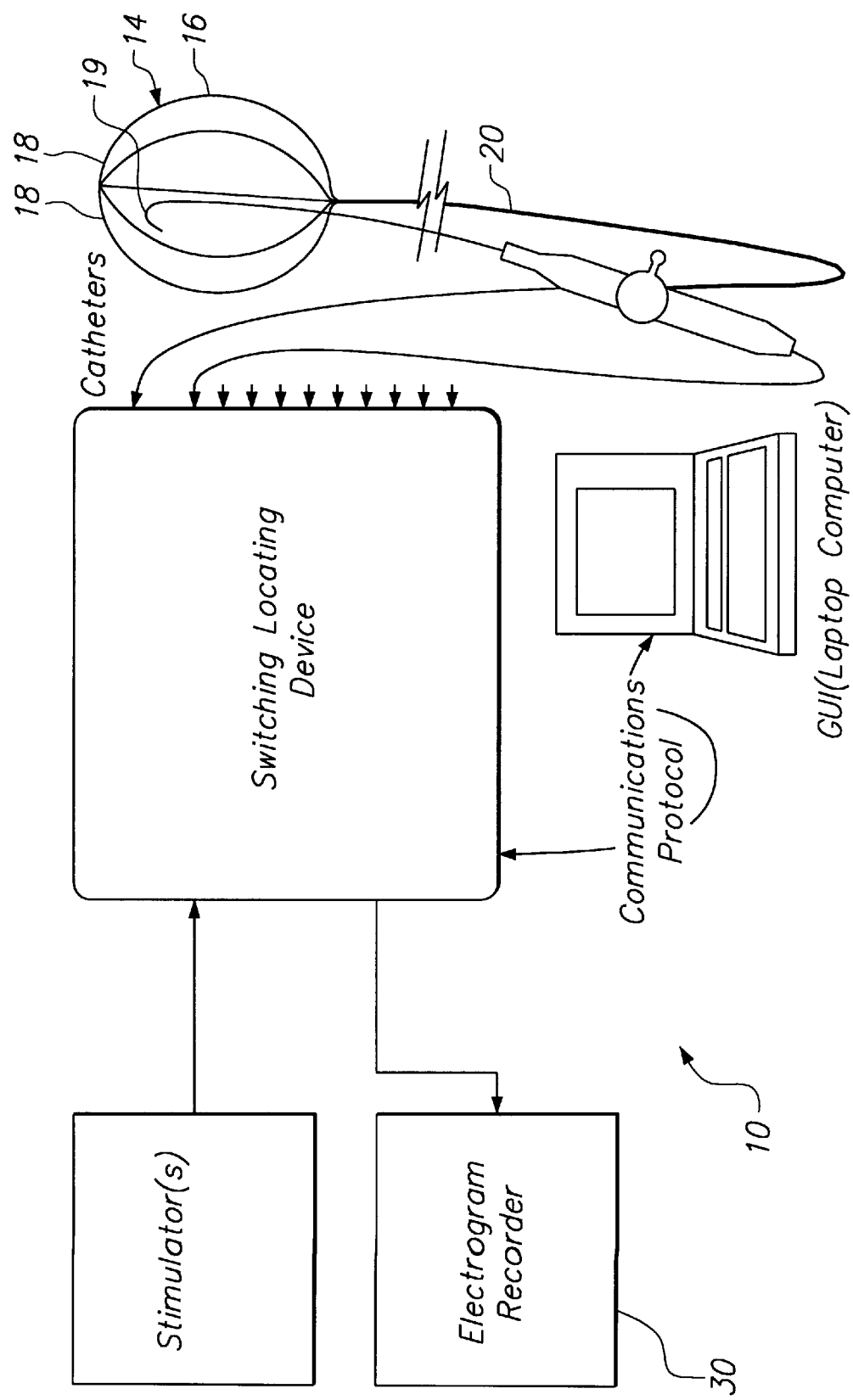
FIG. 2 is a further simplified block diagram of the system shown in FIG. 1.
Figure 3:
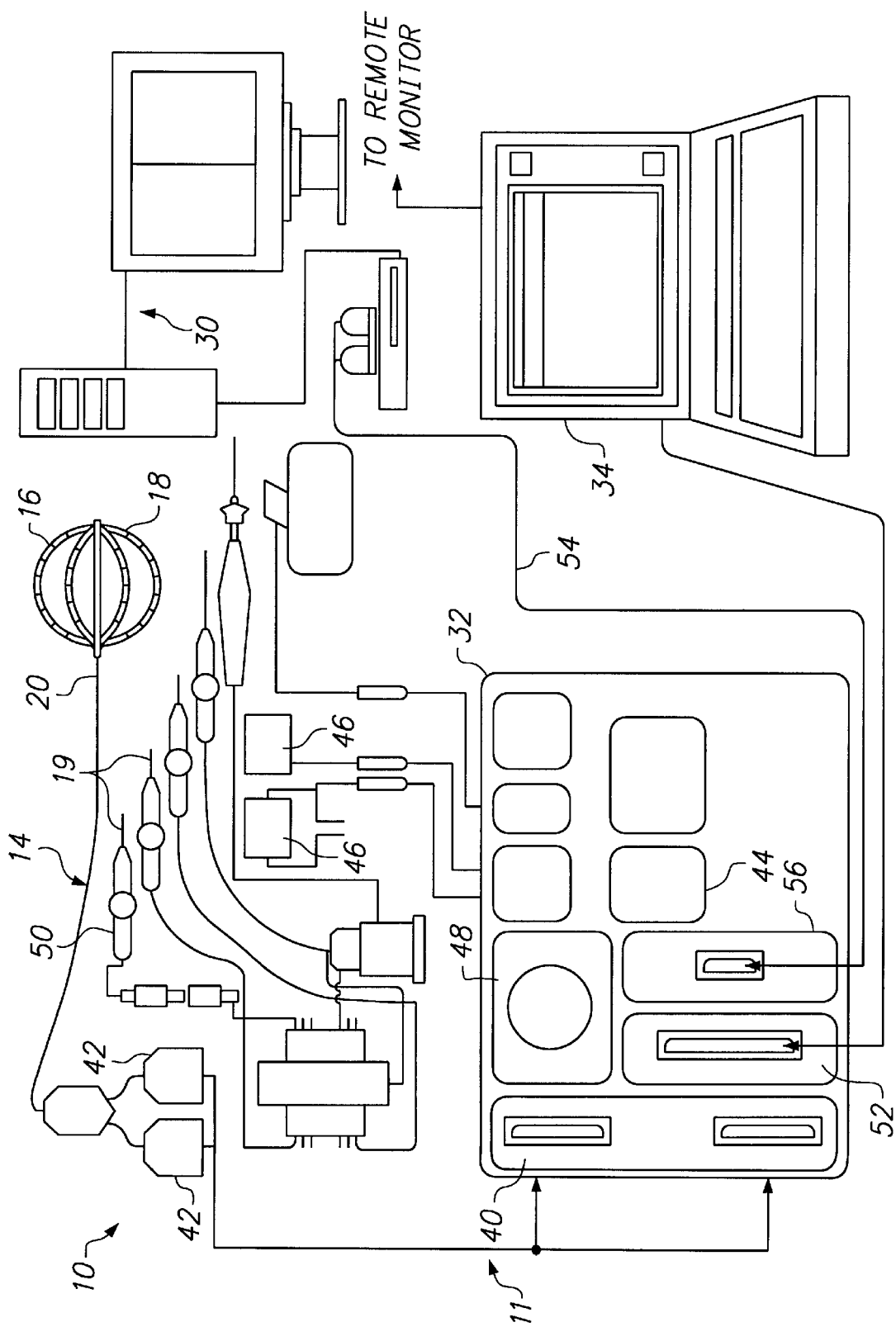
FIG. 3 is a simplified system diagram of a cardiac diagnostic system having a multiple electrode cardiac catheter, an biological recorder system and an interface unit having a unified switching system that couples the catheter with the biological recorder and that embodies various aspects of the invention.

Referring to FIGS. 1, 2 and 3, a system 10 for diagnosing, treating or otherwise administering health care to a patient 12 using a multielectrode catheter 14 is shown. In the illustrated embodiment, the system 10 comprises a cardiac diagnostic system that can be used to diagnose and treat abnormal cardiac conditions, such as arrhythmias. It will be appreciated, however, that the system 10 is illustrative and that the invention can be practiced in settings other than cardiac care.

As illustrated, the system 10 includes a multielectrode catheter 14 deployable within the heart of the patient 12. The catheter 14, which can comprise a catheter of the type shown in co-pending application Ser. No. 08/587,251, filed Jan. 16, 1996, now U.S. Pat. No. 5,647,870 entitled Multiple Electrode Support Structure and commonly owned by the assignee hereof, includes up to sixty-four individual electrodes 16 disposed on a plurality of splines 18. Each of the electrodes 16 is connected to an individual conductor in a multiple conductor cable 20. The cable 20 terminates in one or more connectors through which electrical connection can be made to the individual conductors and, hence, to the individual electrodes.

The system 10 also includes a fluoroscope 22 (FIG. 1) of known construction that can be used to monitor the position of the catheter 14 in the body. The fluoroscope 22 includes a head 24 that generates and directs X-rays into the body, a sensor and an image intensifier 26 that detects the X-rays passing through the body, and a screen 28 that displays the resulting images. The fluoroscope 22 can be rotated around the patient's body to obtain views from different viewing points or "fluoro angles."

The system 10 further includes a biological recorder 30 of known construction that broadly functions to record, store, analyze and display signals acquired by the electrodes 16 of the catheter 14. The biological recorder 30 includes a recording/processing unit that records and processes acquired signals and further includes a display unit that displays the acquired signals to the attending health care personnel.

The system 10 further includes an interface system 11 embodying various aspects of the invention that interfaces the various physical elements of the diagnostic/therapeutic system 10 with each other and with the attending personnel. As will be described in greater detail below, the interface system generally includes an interface unit 32 (FIG. 3) and a graphical user interface (GUI) that tie the various hardware elements of the system 10 together and that enable the attending personnel to interact with the system in a convenient, meaningful way.

The interface unit 32 enables information acquired by the multiple electrodes 16 to be loaded into the biological recorder 30. To this end, the interface 32 functions broadly to couple individual electrodes or groups of electrodes to the biological recorder. By so coupling the electrodes, it is possible to route all the acquired data into the biological recorder even though the number of available inputs into the recorder may be less than the total number of electrodes.

The interface unit 32 also applies a known electrical field through a roving electrode 19 and measures the potential distribution generated at the electrodes 16. This information is then used to estimate the location of the roving electrode 19. A system and method for determining the location of an electrode within body has been disclosed in co-pending application Ser. No. 08/745,795 allowed no patent number yet filed Nov. 8, 1996 entitled "Systems and Methods for Locating Guiding Operative Elements Within Interior Body Regions" and application Ser. No. 08/679,156 filed Jul. 12, 1996, now U.S. Pat. No. 5,722,402 entitled "Systems and Methods for Guiding Movable Electrode Elements within Multiple Electrode Structures" and commonly owned by the assignee hereof. Other methods of localizing electrodes could be employed by those skilled in the art such as presented in prior art U.S. Pat. No. 5,558,091.

The interface unit 32 is also coupled to an external, user-actuatable, microprocessor-based computer control such as a laptop computer 34 having a keyboard 36 and display screen 38. Preferably, a mouse 39 is included with the computer 34. The interface unit operates under the command of the computer 34 to interconnect individual electrodes 16 with individual inputs to the biological recorder 30. The Interface unit also communicates back to the computer 34 information about the location of the roving electrode 19. The computer 34, in turn, responds to requests and instructions entered onto a keyboard 36 by the health care personnel and commands the interface unit 32 to switch among the electrodes 16 as required to achieve the desired function. Commands to configure/test the unified switching system are issued by the computer 34 through the keyboard 36.

The computer 34 receives roving electrode location information from the interface 32 preferably via a serial bus such as RS 232. The location information can comprise three numbers indicating the 3-D coordinates of the roving electrode. Alternatively, it can be a data stream of 64 bits with one bit corresponding to each of the 64 electrodes 16 of the multiple electrode structure 14. A bit equal to logic 1 indicates that the particular electrode 16 resides at less than a predefined distance threshold (e.g. 2 mm) away from the roving electrode 19. A bit equal to logic 0 indicates that the particular electrode 16 resides at more than the predefined distance threshold away from the roving electrode 19. As such, the approximate location of the roving electrode 19 can be retrieved by knowing in the proximity of which of the electrodes 16 the roving electrode resides.

Functions of the Interface System

The interface system 11 performs several functions that make it easier for the attending medical personnel to use the multiple electrode catheter and peripheral equipment with effectiveness and to interpret the resulting data with ease. The various functions provided by the interface system include the following:

RECORDING CONFIGURATION. In this function, the interface system operates broadly to define or configure subgroups among the available electrodes of the multiple electrode catheter and to feed data from the subgroups to the EP recorder for recording. By so configuring the electrodes, an EP recorder having a lesser number of input channels than the number of electrodes on the catheter can nevertheless be effectively used to record and process signals obtained by the catheter. Total flexibility is provided enabling the attending personnel to configure the electrodes for recording in any combination or grouping. Additionally, certain standard or otherwise preestablished groupings or configurations can be implemented as default or standard settings.

PACING CONFIGURATION. In the pacing configuration function, the interface system operates to send pacing signals or pulses to the patients' heart through selected ones or groups of electrodes in the multiple electrode catheter. Again, flexibility is provided enabling the attending personnel to configure the electrodes for pacing as desired. Again, standard or otherwise preestablished groupings or pacing configurations can be defined and implemented. The pacing pulses themselves can be applied to the patient's heart through dedicated pacing electrodes. Alternatively, the pacing pulses can be applied through any of the electrodes of the multiple electrode catheter in a "retrograde" fashion. The pulses themselves can be generated in one or more external units and coupled to the interface unit through appropriate inputs. The interface unit directs the pacing pulses to selected ones of the electrodes in accordance with the instructions of the attending personnel.

SEQUENCE OF RECORDING CONFIGURATIONS. In the sequence of recording configurations operating mode the interface system cycles through a predetermined sequence of predetermined recording configurations. The specific recording configurations can be and preferably are specified in advance, as is the particular sequence or order in which the individual recording configurations are implemented. This function enables the attending personnel to design or designate the order and manner in which the individual electrodes of the multiple electrode catheter convey signals or data from the patient's heart to the EP recorder. Through appropriate use of the sequence of recording configurations function, all the available electrodes can supply information to the EP recorder even though the number of electrodes exceeds the number of available input channels to the EP recorder.

SEQUENCE OF PACING CONFIGURATIONS. The sequence of pacing configurations function is similar to the sequence of recording configurations function except that the interface sequentially cycles through a predetermined series of pacing, rather than recording, configurations. This enables the attending personnel to pace the heart through any of the available electrodes in a predetermined manner.

THREE DIMENSIONAL NAVIGATION OF THE ROVING ELECTRODE. In this function, the interface serves to help the attending personnel locate an additional or roving electrode relative to the electrodes of the multiple electrode catheter and the patient's heart.

The Interface Unit

The interfacing system 11 enables information acquired by the multiple electrodes 16 to be loaded into the biological recorder 30. To this end, the interfacing system functions broadly to couple individual electrodes or groups of electrodes 16 to the biological recorder 30. By so coupling the electrodes, it is possible to route all the acquired data into the biological recorder even though the number of available inputs into the recorder may be less than the total number of electrodes.

The interfacing system 11 includes the interface unit 32 that is coupled between the catheter 14 and biological recorder 30. The interface unit 32 is also coupled to an external, user-actuable, microprocessor-based computer control such as the laptop computer 34. The interface unit 32 operates under the command of the computer 34 to interconnect individual electrodes 16 and 19 with individual inputs to the biological recorder 30. The computer 34, in turn, responds to requests and instructions entered onto the keyboard 36 by the health care personnel and commands the interface unit 32 to switch among the electrodes 16 and 19 as required to achieve the desired function. Commands to configure/test the unified switching system are issued by the computer 34 through the keyboard 36.

It will be appreciated that the computer 34 can be programmed with pre-determined protocols that correspond to higher level commands entered on the keyboard 36 and that, when implemented, achieve the desired function. In this manner, the health care personnel need not concern themselves with the specifics of which electrodes are connected to which inputs of the biological recorder. Instead, the personnel can simply enter the control function they desire to achieve and the computer 34 and interface unit 32 then switch among the electrodes and inputs as needed to achieve the desired function. Because of the flexibility in programming provided by the computer 34, a variety of catheters can be successfully interfaced with a variety of biological recorders.

As further illustrated in FIG. 1, the interface unit 32 is provided with a plurality of input and output ports for connection to external devices. A first port 40 is provided for connection to the cardiac catheter 14. This port 40 accepts the connectors 42 of the catheter 14. Two additional ports 44 are provided for connection to up to two external pacing pulse generators or stimulators 46. Pacing pulses generated by the external pacing pulse stimulators 36 can be selectively coupled to any of the available cardiac electrodes 16 and 19 to permit cardiac pacing through any of the electrodes 16. Still additional ports 48 permit connection to diagnostic catheters 50. Still another port 52 is provided for connection to the biological recorder 30. A suitable cable 54 is provided and is made up on a "custom" basis depending upon the particular type of biological recorder that is used. Finally, still another port 56 is provided for connection to the computer 34.

Referring to FIG. 4, the interface unit 32 is centered around an application specific integrated circuit (ASIC) 58. Such an ASIC appropriate for use in the interface system and interface unit is shown and described, for example, in U.S. application Ser. No. 08/770,971, now abandoned, entitled, "Unified Switching System for Electrophysiological Stimulation and Signal Recording and Analysis," filed Dec. 12, 1996 and commonly owned by the assignee hereof, the specification of which is incorporated by reference herein. The interface unit 32 includes a microprocessor-based interface 60 that serves as an interface between the external laptop computer 34 and the ASIC 58. The microprocessor interface 60, in response to high level instructions received from the laptop computer 34, generates appropriate control commands that are applied to the ASIC 58 to achieve the desired function. The various catheter electrodes 16, 19 are coupled to the ASIC 58 through appropriate catheter interface circuitry 62 that functions, broadly, to isolate the ASIC 58 from potentially damaging signals, currents and voltages that might be encountered by the various electrodes in the course of treating a patient. Such potentially damaging signals can include, for example, high voltage pulses externally applied to the patient's chest during the course of defibrillation. As illustrated, the ASIC 58 is also coupled to the external stimulators 46 and to the biological recorder 30.

Figure 5:
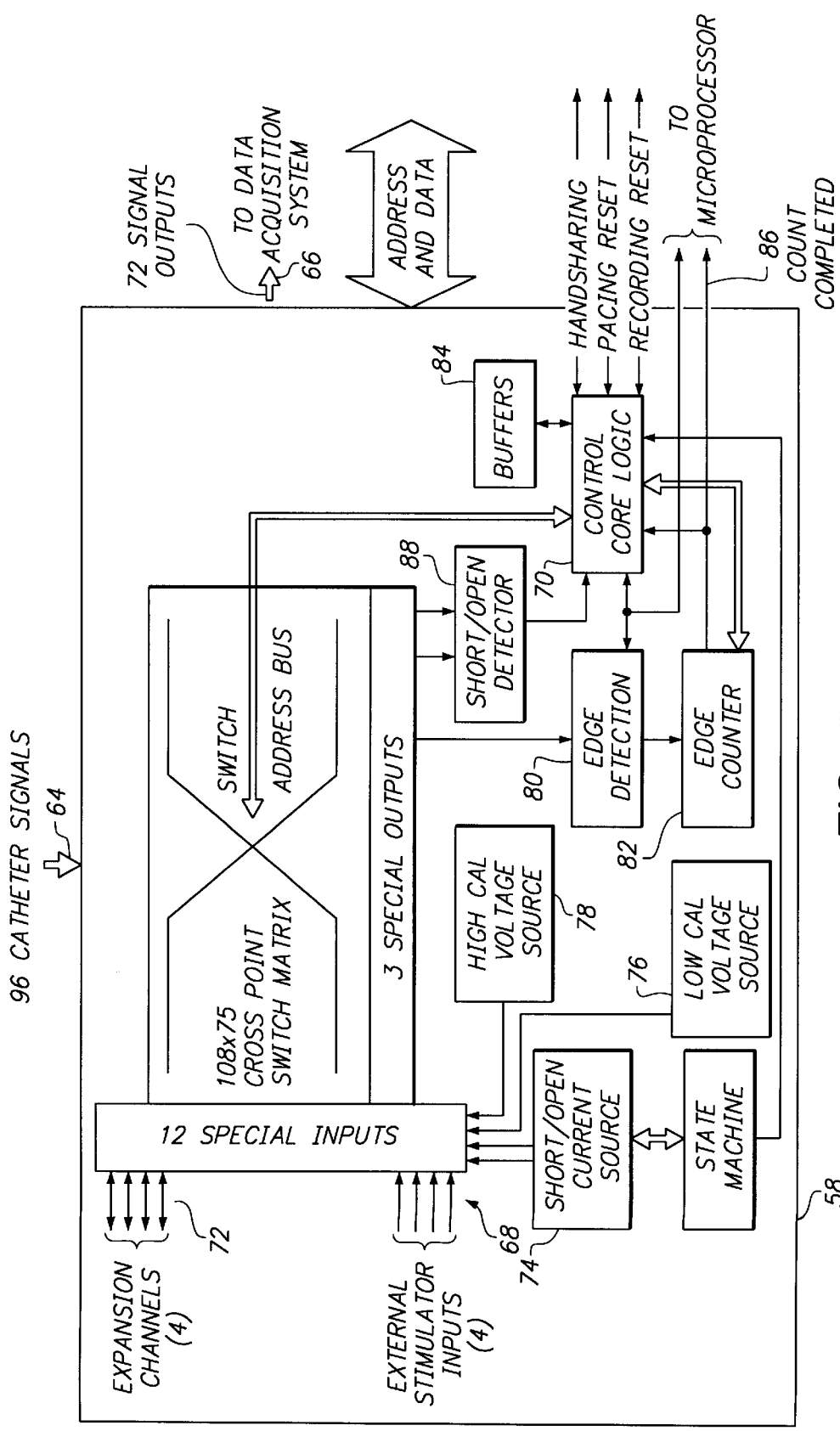
FIG. 5 is a block diagram of an application specific integrated circuit (ASIC) useful in implementing the interface unit shown in FIGS. 1–3.

Referring further to FIG. 4 and the ASIC system block diagram of FIG. 5, the ASIC 58, in the illustrated embodiment, includes ninety-six primary analog input pins 64 and seventy-two analog output pins 66. The ASIC 58 further includes four additional analog input pins 68 through which high level external signals, such as those produced by the external stimulators 46, can be received.

In general terms, the interface unit 32 is capable of providing various functions. For example, any of the input pins 64 of the ASIC 58 can be connected to any of the output pins 66. This enables various subsets of the electrodes 16, 19 to be connected to various subsets of the biological recorder inputs. In addition, any of the additional input pins 68 can be coupled to any of the primary input pins 64. This permits pacing pulses generated by any of the external stimulators 46 to be applied to the heart through any of the cardiac electrodes 16, 19. Finally, the interface unit 32 is capable of switching high level pacing pulse signals "backwardly" from any of the ASIC output pins to any of the input pins so as to permit "retrograde" pacing back through the interface unit 32. Pacing can thus be supported either from external pacing stimulators or from biological recorders that have pacing output capabilities.

Referring further to FIG. 5, the ASIC 58 comprises a 99×80 cross point switch matrix that is controlled by an on-chip control and core logic circuit 70. The control/core logic circuit 70 responds to commands generated by the microprocessor interface 60 in response to higher level commands received from the computer 34 and configures the cross point switch matrix so as to establish desired electrical connections between the various electrodes, the external pacing stimulators 46 and the biological recorder 30. In addition, the interface unit 32 performs such other functions as detecting open or shorted electrodes, counting applied pacing pulses, electrode identification and confirmation of correct system connections.

As further illustrated in FIG. 5, four expansion channels 72 are provided for implementing an impedance mapping function of the type shown and described in connection with FIGS. 9(a) and 9(b) below. The expansion channels serve the purpose of applying and measuring signals needed for such impedance mapping. A constant current source 74 is provided for implementing an on chip test for open or shorted electrodes. A low voltage identification source 76 and a high voltage identification source 78 are also included. A pulse detection circuit or pulse detector 80 is provided for detecting the leading or trailing edges of pacing pulses applied through the interface unit 32, and an up/down edge counter 82 is provided for counting the number of pulses thus detected. In the preferred embodiment, the trailing edge is detected. Various buffer registers 84 are provided for system control and are coupled to the control/core logic 70.

As previously noted, signals can be transferred bidirectionally between the inputs and outputs, and pacing pulses can be applied "backwardly" through the interface unit 32 in "retrograde" fashion from any of the output pins 66 or external stimulator inputs 44 to any of the input pins 64. To avoid the possibility of switching among the various pins 64, 66 and 44 while a pacing pulse is being applied, the interface unit 32 preferably includes an edge detection and switch inhibition capability. To this end, the edge detector 80 senses the leading or rising edge of each pacing pulse and provides a signal each time the leading edge of a pulse is detected. The signal thus generated is used to inhibit switching of the cross point switch matrix while the pacing pulse is present. This ensures that the full width of the pacing pulse is delivered to the desired electrode and helps reduce the possibility of inducing ventricular fibrillation. Alternatively, switching may be forced to occur within a specified time after the trailing edge of the pacing pulse.

The pulse counter 82 responds to the pulse detection signals generated by the pulse detector 80 and increments or decrements the count in the counter 82 with each signal. In the illustrated embodiment, the counter is an eight bit counter and, hence, can support a count between zero and 255. The counter is under the control of the control/core logic 70 and, ultimately, the computer 34 and can be enabled or disabled by the computer 34 as desired or required. The interface unit 32 preferably supports reading/writing the count in the counter 82 without interruption of the count in progress. The ASIC 58 includes an output pin 86 for signaling the computer 34 when the count has been completed, i.e., has reached zero or 255.

In accordance with another aspect of the invention, the interface unit 32 provides for automatic detection of open or shorted electrodes. Given the large number of electrodes 16 that can be used in a mapping or pacing procedure, it is possible that one or more of the electrodes can be shorted or open. The short/open test function provided by the interface unit 32 helps alert the attending health care personnel to the existence of such malfunctions.

To provide for automatic short/open testing, the short/open current source 74 included in the ASIC 58 comprises a constant current source that can be selectively switched to each of the cardiac electrodes 16 under the command of the computer 34. In the event any of the electrodes is open, a high voltage condition will result when the constant current source 74 is coupled to that electrode. A short/open detector 88, which is also coupled to the electrodes along with the source 74, detects the occurrence of such a high voltage condition and interprets it as an open electrode. An appropriate signal is returned to the computer 34 which, in turn, generates an appropriate display for the attending personnel. The display preferably identifies which electrode is open. In the case of a shorted electrode, an abnormally low voltage results when the constant current source 74 is coupled to the electrode. Again, the short/open detector 88 detects the abnormal condition and signals the computer 34, which generates an appropriate display.

The high voltage source 78 and low voltage source 76 are also individually coupled to the outputs 66 under the control of the computer 34. The voltages thus applied to the outputs 66 can be used for identification of signals as well as for visual confirmation of correct connections by the operating personnel.

Figure 6:
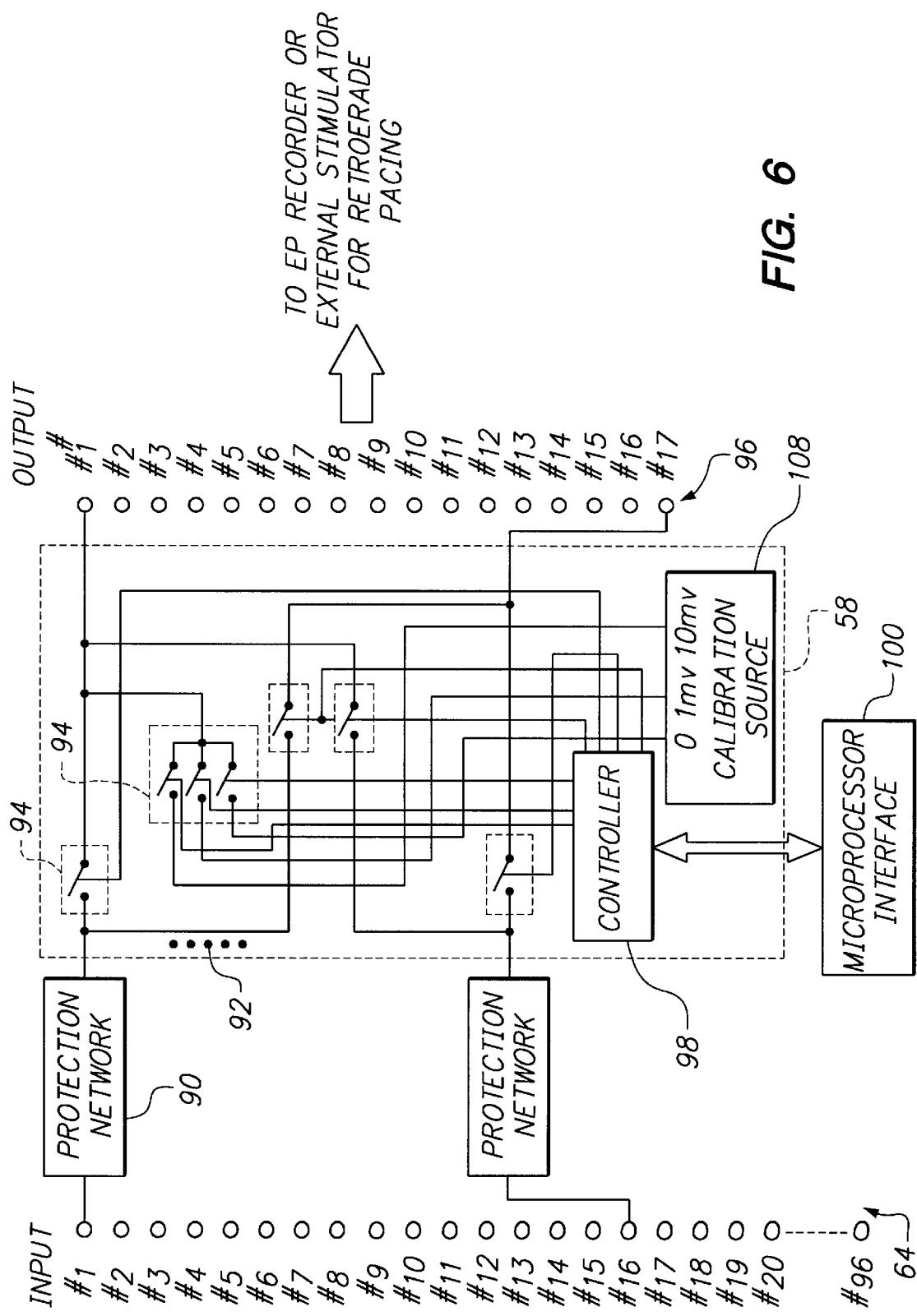
FIG. 6 is a functional block diagram of the ASIC shown in FIG. 5 useful in understanding the switching functions provided by the ASIC in a recording mode when the ASIC is used to interconnect a multitude of available electrodes with a sixteen channel biological recorder system.

Operation of the system 10 in an electrode configuration mode can best be understood by reference to FIG. 6. As illustrated, each of the ninety-six individual inputs 64 is coupled through a protection network 90 to an input pin 92 of the ASIC 58. Within the ASIC 58, each input pin 92 is coupled through a separate, individually controllable switch 94 to each of a plurality of output pins 96 on the ASIC 58. Preferably, this function is implemented using a cross-point switch matrix (FIG. 5). Each of the switches 94 is under the control of a controller 98 that, in turn, is controlled by a microprocessor interface 100. The controller 98 actuates individual ones of the switches 94 so as to controllably connect any of the input pins 92 with any of the output pins 96. Accordingly, depending upon which of the switches 94 is actuated by the controller, any of the inputs 64 can be coupled to any of the outputs 96.

As further illustrated, each output pin 96 is also coupled through three independent, separately controllable switches 102, 104 and 106. to the zero, low and high voltage identification signal sources (collectively, reference numeral 108). Each of the switches is independently controlled by the controller 98. Accordingly, the controller can controllably and independently apply the zero volt, low voltage or high voltage identification signal to any of the output pins 96. It will thus be appreciated that the interface unit 32 in this manner provides complete flexibility in coupling any of the input pins 92 to any of the output pins 96 and in coupling any of the identification signal sources 108 to any of the output pins 96.

System Operation

Figure 7:
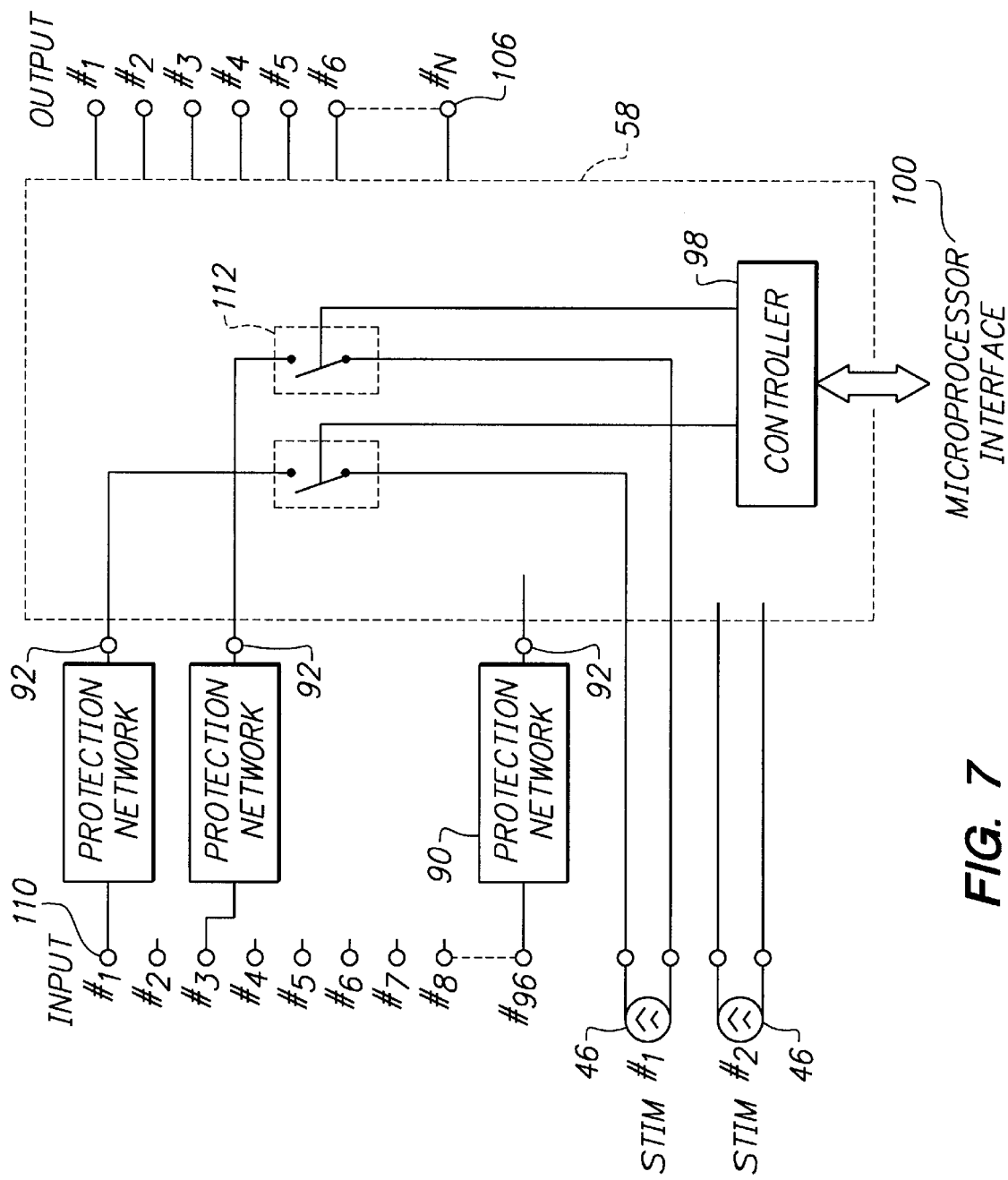
FIG. 7 is a simplified functional block diagram of the ASIC showing the ASIC in a pace switching, detection and counting mode.

Operation of the system 10 in a pacing mode can best be understood by reference to FIG. 7. As illustrated, the external stimulators 46 are connected to the interface unit 32 through input pins 110. Each of the input pins 110 is coupled through a separate, individual, controllable switch 112 to each of the input pins 92. Each of the switches 112 can be separately actuated under the control of the controller 98 to couple the principal terminals of either stimulator 46 to any pair of input pins 92 and, thus, to any pair of electrodes connected to those particular input pins 92. Again, the controller 98 responds to commands generated by the computer 34 and applied to the ASIC 58 through the microprocessor interface 100.

Figure 8A:
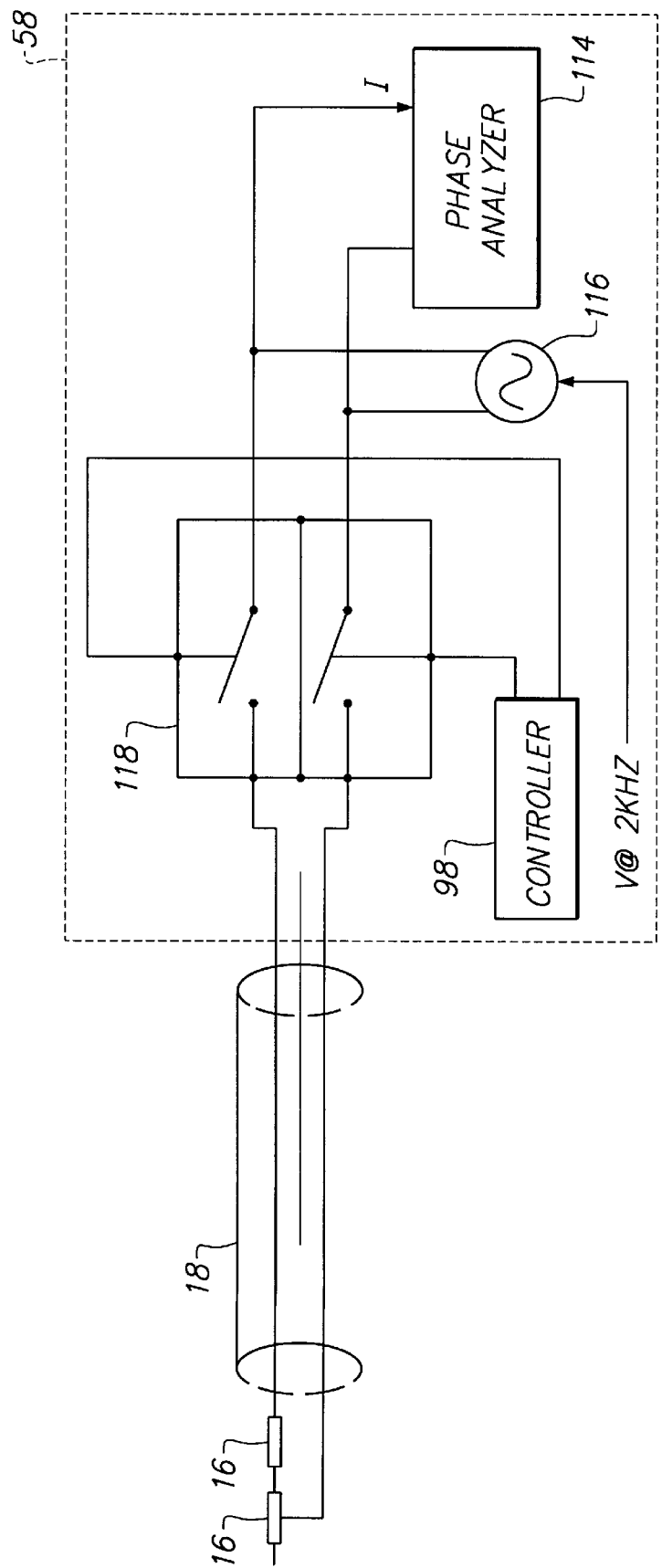
FIGS. 8(a) and 8(b) are, respectively, a simplified block diagram and a logic flow chart diagram useful in understanding the operation of the unified switching system in a short/open detection mode.
Figure 8B:
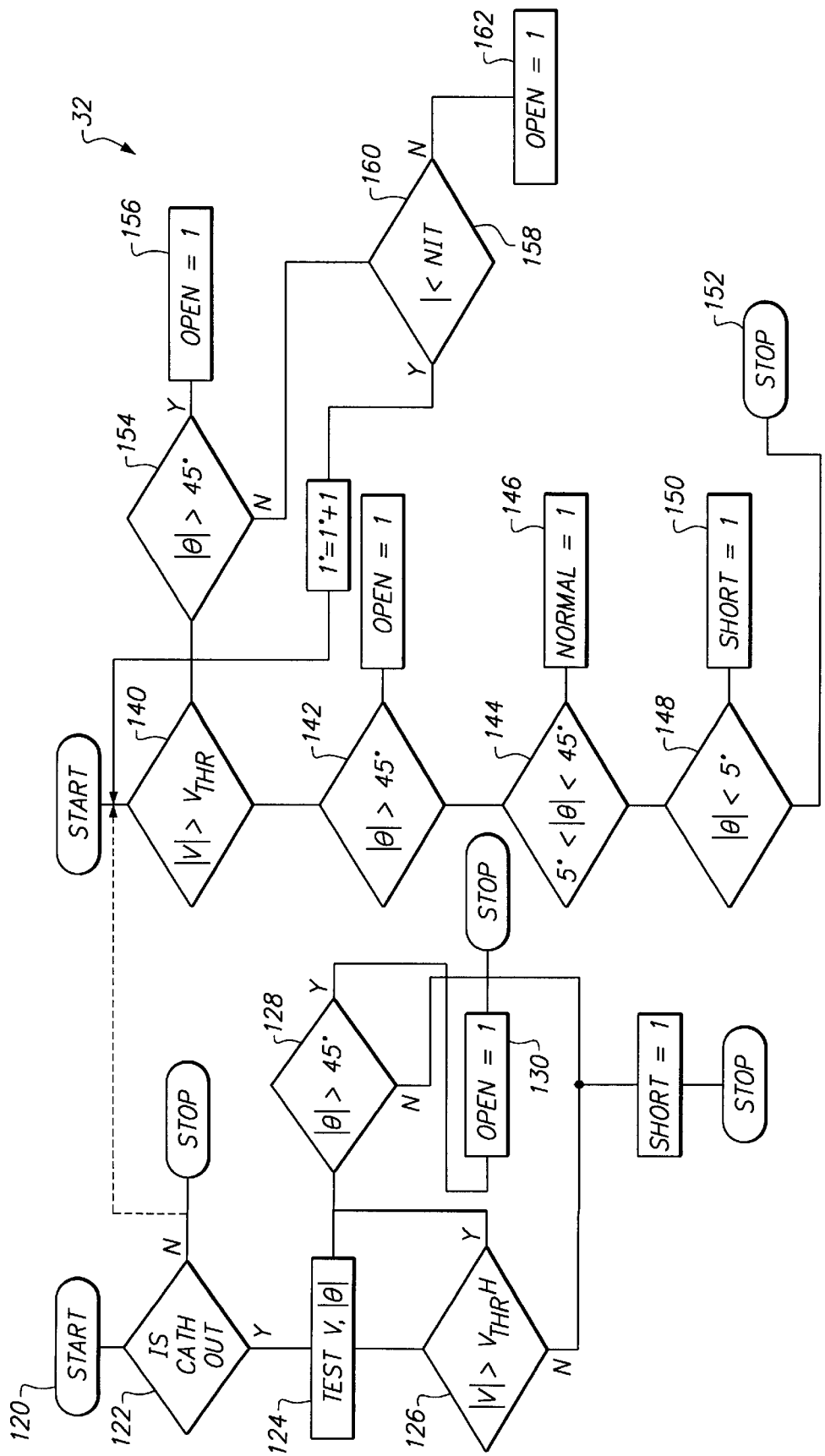

Operation of the system 10 in a short/open detect mode can best be understood by reference to FIGS. 8(a) and 8(b). As illustrated in FIG. 8(a), a phase analyzer 116 is provided in addition to a constant frequency voltage source 114. Preferably, the voltage source 114 is a sine wave generator. Other waveforms, such as pulsed, rectangular or triangular, could be used. Preferably, the frequency of the signal generated by the source 114 is 2 kHz., and the current is less than 20 $\mu$A for safety. As illustrated, the voltage source 114 and phase analyzer 116 are connected to the electrodes through individually actuable switches 118 associated with each of the input pins 92 (FIG. 6). The switches 118, in turn, are under the control of the controller 98 that, by actuating selected ones of the switches 118, can couple the voltage source 116 and phase analyzer 114 to any of the electrodes 16. It will be appreciated that, for purposes of this description, the controller 98 incorporates and integrates the functions of the control/core logic 70, the edge detector 80 and the edge counter 82. Similarly, it will be appreciated that the microprocessor interface 100 incorporates and integrates the functions of the high and low identification voltage sources 76 and 78.

The operational logic used in sensing open and shorted electrodes is illustrated in the logic flow chart of FIG. 8(b).

The system 10 is operable to test the status of the various electrodes both before and after the catheter 18 is placed in a patient's body. After the test sequence is initiated (box 120), the system verifies whether the catheter is in or out of the patient's body (122). If the catheter is outside the patient's body, the system then applies the alternating current to the electrodes in a preselected sequence and senses the resulting voltages and phase relationships (124). If the magnitude of the resulting voltage exceeds a pre-determined upper threshold $V_{thrH}$ (126), the system then checks whether the phase $\phi$ is greater than a predetermined limit, which, in the illustrated embodiment, is 45° (128). If both criteria are met (i.e., $|V| \geq V_{thrH}$ and $\phi \geq 45°$), an open electrode condition is indicated (130).

If it is determined at step 122 that the catheter is in place within the patient's body, the system then operates in a somewhat different mode. The alternating current is applied to the electrodes and the resulting voltage and phase are noted. If the resulting voltage is less than a predetermined threshold $V_{thr}$, (140) the system then checks to see whether the phase $\phi$ is less than a predetermined upper limit, which, in the illustrated embodiment, is, again, 45° (142). If the measured phase is less than the 45° limit, the system next checks to see whether the phase is between the 45° upper limit and a predetermined normal lower limit, which, in the illustrated embodiment, is 5° (144). If the measured voltage V is less than the threshold $V_{thr}$, and the measured phase $\phi$ is between the 45° and 5° upper and lower limits, then normal electrode operation is indicated (146). If the measured phase is less than the 5° lower limit (148), a shorted electrode condition is indicated (150) and further testing is stopped (152).

If the measured voltage V is determined to be above the threshold $V_{thr}$ at step 140, the system performs additional checks before concluding that the electrode is open. In particular, after determining that $|V|>V_{thr}$ at step 140, the system then compares the measured phase $\phi$ against the 45° upper limit (154). If $\phi>45°$, then an open electrode condition is indicated (156). However, if $\phi<45°$, system operation returns to step 140 where the measured voltage V is once again compared to the threshold $V_{thr}$. At the same time, a pointer i is initially set to "1" and is compared against a predetermined end point integer $N_{it}$ (158). If the current value of i is less than the end point integer $N_{it}$, system operation returns to step 140 where the measured voltage is once again compared to the threshold $V_{thr}$. If, this time, V is below the threshold, operation proceeds to step 142. If V remains above the threshold, the measured phase $\phi$ is once again compared against the 45° upper limit at step 134 while the pointer i is incremented by one. If this time the measured phase is above the 45° upper limit (154), an open electrode condition is indicated (156). If the measured phase $\phi$ is below the 45° upper limit (154), system operation returns once again through step 158 to step 140. At the same time, the incremented pointer i is again compared against the end point integer $N_{it}$ (158). Operation in this "loop" mode continues until such time as (A) the measured phase $\phi$ exceeds the 45° upper limit (154) and an open electrode condition is indicated, (B) the measured voltage V remains above the threshold $V_{thr}$ for a number of cycles sufficient to increment the pointer i to the end point integer $N_{it}$ (160) and thereby confirm an open electrode condition (162) or (C) the measured voltage V drops below the threshold $V_{thr}$ as determined at step 140. Such operation helps guard against false indications of open electrodes.

Figure 9A:
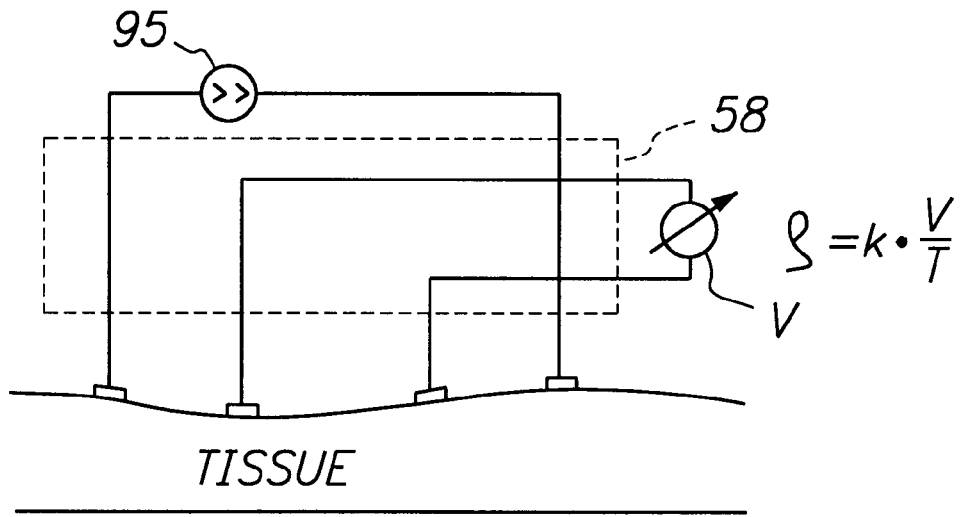
FIG. 9(a) is a simplified functional diagram illustrating on example of a four-electrode impedance mapping technique wherein the ASIC is used.
Figure 9B:
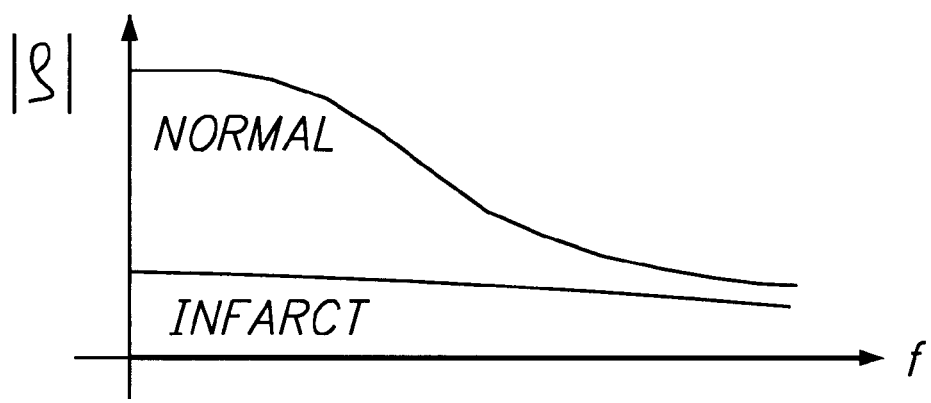
FIG. 9(b) is a graph showing measured impedance vs. frequency for both normal and infarcted cardiac tissue.

Operation of the system 10 in an "impedance mapping" mode can best be understood by reference to FIGS. 9(a) and 9(b). In the impedance mapping mode, a variable frequency AC current is applied from a source 95 through the interface 32 and electrodes 16 to the tissue of the heart. The frequency of the applied current is changed and the applied current and resulting voltage across the cardiac tissue is measured. The resistivity (ρ) of the cardiac tissue is determined according to the relationship ρ=K·(V/I) where K is a constant, I is the applied current and V is the resulting voltage. As illustrated in FIG. 9(b), normal cardiac tissue is characterized in that the resistivity of the tissues drops with increasing frequency while infarcted tissue maintains a relatively constant resistivity largely independent of frequency. Accordingly, by applying an alternating current of changing frequency to the cardiac tissue and monitoring the resulting resistivity, areas of infarcted cardiac tissue can be located and differentiated from areas of normal cardiac tissue.

Figure 10A:
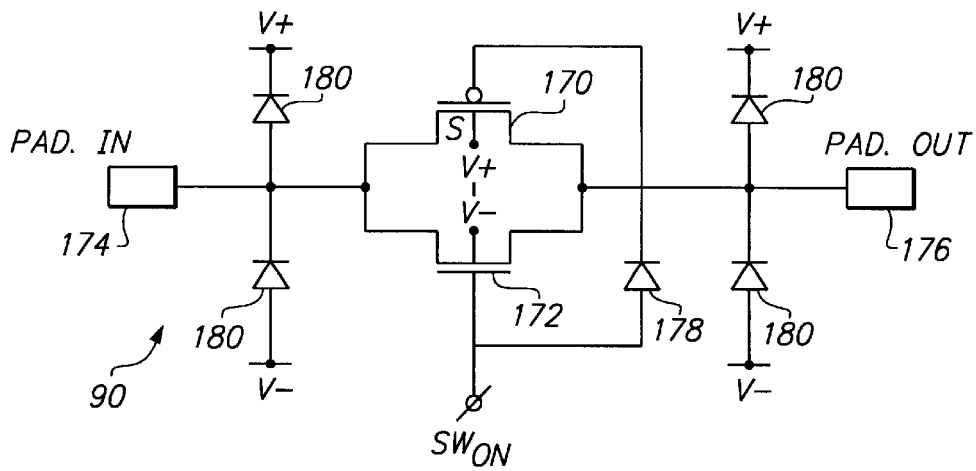
FIG. 10(a) is a simplified schematic diagram of a CMOS transmission gate used in implementing one embodiment of the ASIC.
Figure 10B:
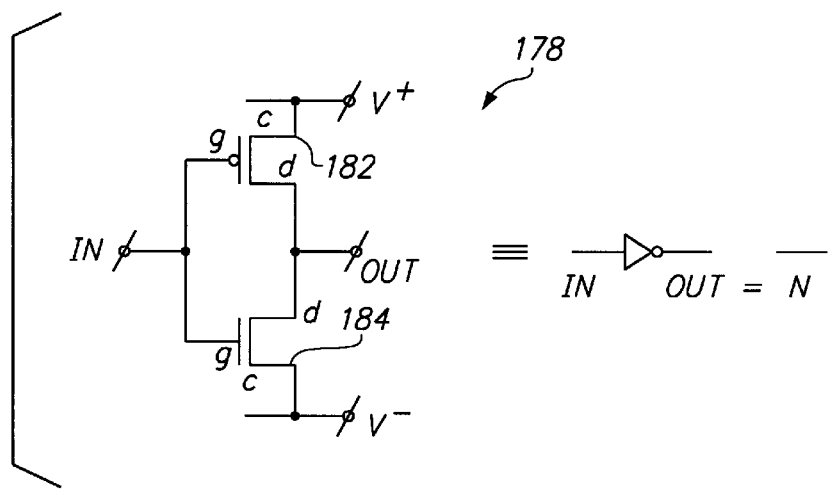
FIG. 10(b) is a simplified schematic diagram of an inverter used in conjunction with the transmission gate shown in FIG. 10(a).

The operation of each of the switches 96 (FIG. 6) in the ASIC 58 can best be understood by reference to FIGS. 10(a) and 10(b). As illustrated, each switch 94 includes a PMOS transistor 170 having its principal electrodes connected in parallel with the principal electrodes of an NMOS transistor 172. The sources and drains of the transistors 170, 172, in turn, are connected between input and output pads 174, 176 associated with each switch 94. A control signal generated by the controller 98 is applied directly to the gate of the NMOS transistor 172 and through an inverter 178 to the gate of the PMOS transistor 170. An appropriately sensed control signal thus applied by the controller 98 enables the PMOS and NMOS transistors 170 and 172 jointly to pass signals in both directions between the pads 174 and 176. It should be noted that, depending upon the magnitude and polarity of the signals applied to the pads 174 and 176, either of the transistors 170 or 172 might be conductive at any instant when the controller 98 signals the switch 94 to turn "on".

As further illustrated in FIG. 10(a), static protection is provided in the form of reverse-biased diodes 180 connected between each of the pads 174 and 176 and the positive and negative polarity voltage sources $V^+$ and $V^-$.

The configuration of each inverter 178 is shown in FIG. 10(b). As illustrated, each inverter 178 includes a pair of MOS transistors 182 and 184 having their principal electrodes connected in series between the positive and negative polarity voltage sources $V^+$ and $V^-$. The input to each inverter 180 is applied simultaneously to the gate of each transistor 182 and 184, and the output of each inverter is obtained between the transistors 182 and 184. A logic "high" voltage applied to the input biases transistor 184 "on" causing the negative polarity source voltage to appear at the output. Similarly, a logic "low" voltage applied to the input biases transistor 182 "on" thereby causing the positive polarity supply voltage to appear at the output. In this manner, the output voltage is opposite the input voltage thereby achieving the inversion function.

Figure 10C:
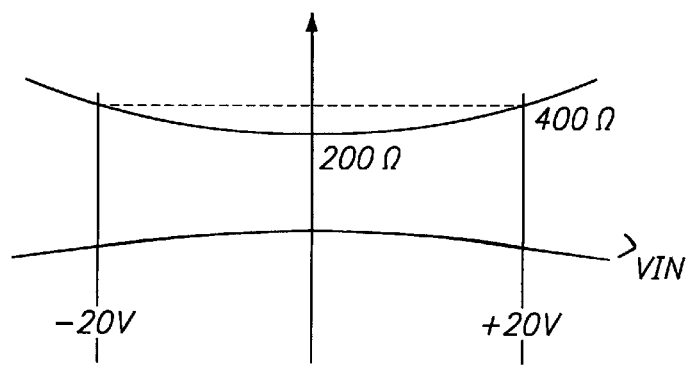
FIG. 10(c) is a graph showing the "on" resistance $R_{on}$ versus input voltage $V_{in}$ for the transmission gate shown in FIG. 10(a).

The transfer characteristics of the switch 94 shown in FIG. 10(a) is shown in FIG. 10(c). As shown, the "on" resistance $R_{on}$ of each switch 94 varies from a low of approximately 200 Ω at an input voltage ($V_{in}$) of 0 volts to approximately 400 Ω at $V_{in}$=+20V and $V_{in}$=−20V.

Figure 10D:
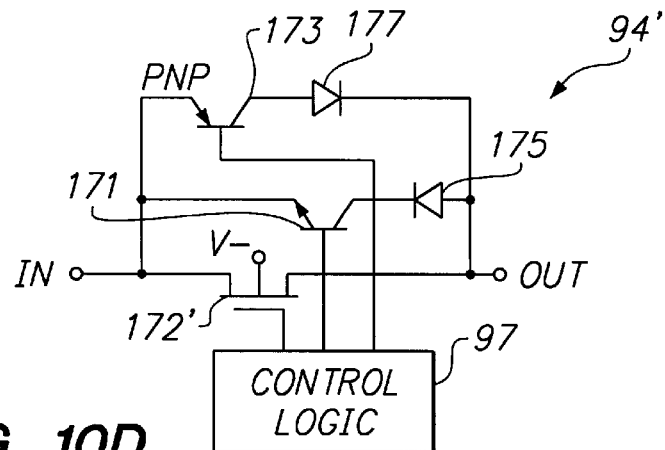
FIG. 10(d) is an alternate embodiment of a transmission gate useful in implementing one embodiment of the ASIC.
Figure 10E:
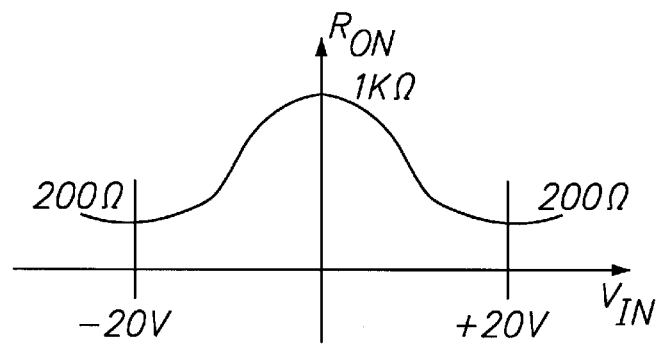
FIG. 10(e) is a graph showing the "on" resistance $R_{on}$ versus input voltage $V_{in}$ for the transmission gate shown in FIG. 10(d).

An alternate form of switch 94' is shown in FIG. 10(d). In this switch 94', the drain and source of an NMOS transistor 172' is shunted by an NPN transistor 171 and a PNP transistor 173. A forward biased diode 175, 177 is series connected with the collector of each transistor 171, 173. The bases of the transistors, as well as the control gate of the NMOS transistor, are coupled to the control logic 97. In this embodiment, maximum switch resistance is obtained when the applied input voltage $V_{in}$ is zero, and minimum switch resistance is obtained when the input voltage $V_{in}$ is at an extreme, i.e., =20 V or −20V. The switch transfer characteristics are shown in FIG. 10(e). As illustrated, the switch on resistance $R_{on}$ is approximately 1 KΩ at $V_{in}$=0 V, and is approximately 200 Ω at $V_{in}$=±20 V.

Figure 11:
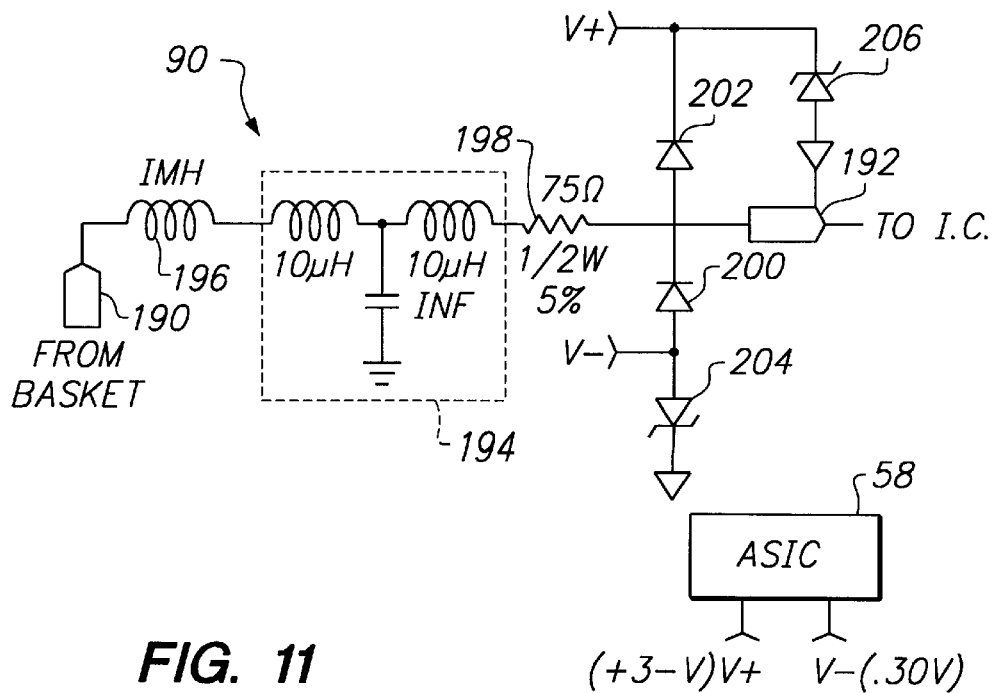
FIG. 11 is a schematic diagram of an external protection network usable in connection with the unified switching system.

The configuration of each protection network 90 is shown in FIG. 11. As illustrated, each protection network 90 includes an input node 190 and an output node 192. A "T" network low pass filter 194 is coupled through an inductor or "choke" 196 to the input node 190 and is coupled through a current limiting resistor 198 to the output node 192. A pair of diodes 200, 202 protect the ASIC inputs 192 from transient high voltages. The diodes 200, 202 connect to the ASIC power supply voltages $V^+$ and $V^-$. Overvoltage protection is provided by means of a pair of zener diodes 204, 206 that shunt to ground any voltages in excess of the zener voltage.

In the illustrated embodiment, the switching function provided by the ASIC 58 is controlled by writing control words to the chip. The control sequence consists of 8 bits of input address, 8 bits of output address and 8 bits of command data. These functions are implemented through an 8 bit microprocessor-compatible bus. Operation of the pulse counter 82 is similar. The control sequence contains 8 bits indicating the count loaded or to be read back with the remaining 8 bits of command data serving to enable or disable the counter and specify whether the counting function is to be up or down. As also illustrated, the ASIC 58 preferably provides a hardware "handshake" function that confirms that applied switching commands have been received and executed.

Figure 12:
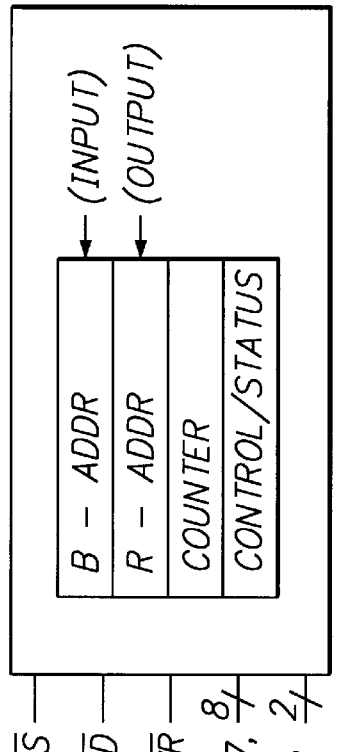
FIG. 12 is a diagrammatic illustration of the internal register structure of the unified switching system.
Figure 13:
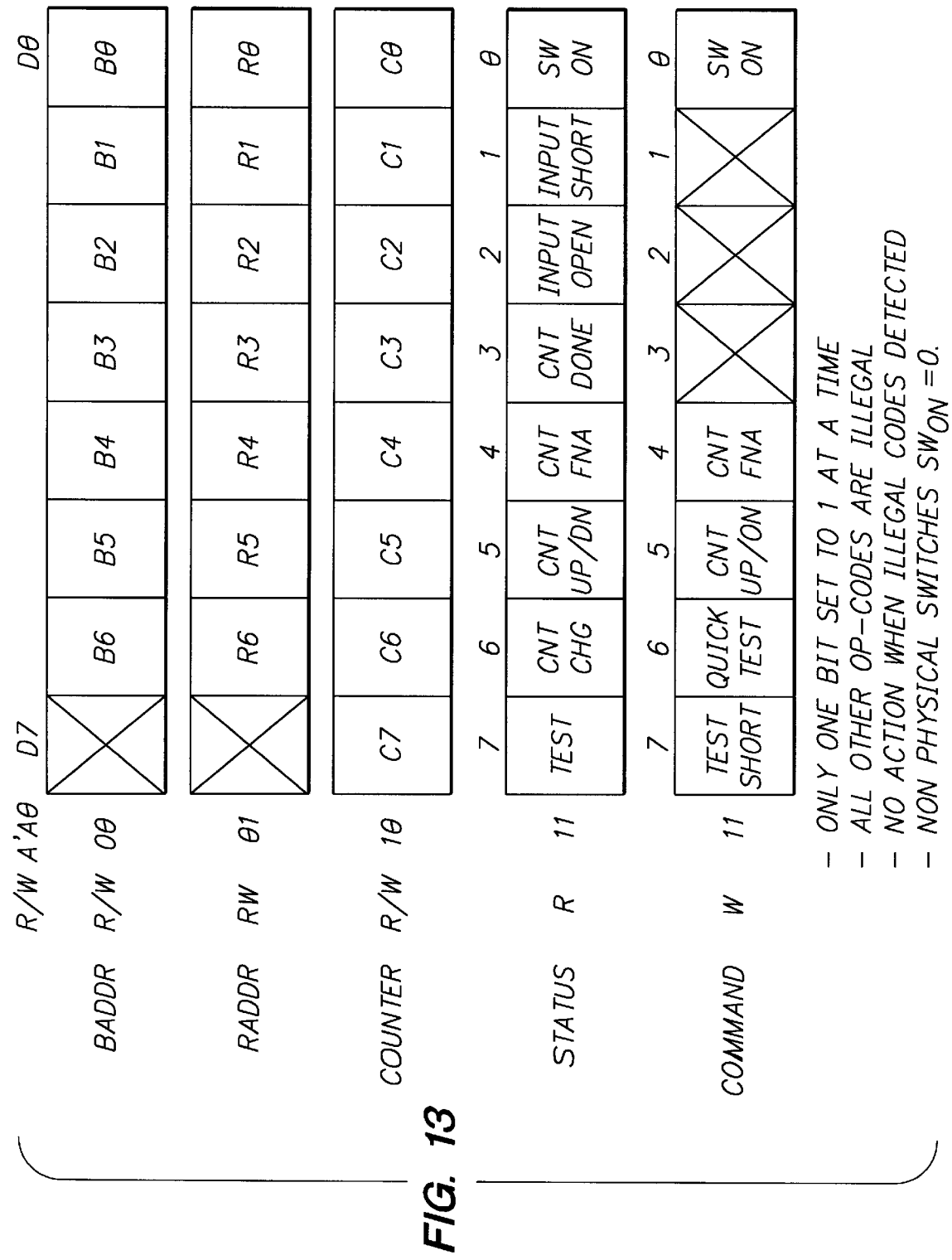
FIG. 13 is a chart showing the instruction sequence used in the unified switching system.

In the illustrated embodiment, communication with the ASIC 58 can best be understood by reference to FIGS. 12 and 13. As illustrated, the ASIC includes four registers for reading data into and out of the ASIC. The first register is a "B-ADDR" register that specifies the ASIC input to be connected. The second register is an "R-ADDR" register that stores the ASIC output to which the selected input connects. The third register is a "COUNTER" register that reflects the current count in the counter. The final register is a "CONTROL/STATUS" register that functions alternately to either receive an external "command" word for controlling ASIC operation or to receive an internally generated "status" word reflecting the current status of a particular system parameter.

As further illustrated, five different types of control inputs can be applied to the ASIC. The first is a "CHIP SELECT" (CS) command that operates to enable and disable the ASIC. The second and third control inputs are respective "READ" (RD) and "WRITE" (WR) commands that control whether data are to be read into or written out of the ASIC. The fourth control input is an eight bit data bus "D0–D7" through which eight bit data words can be written into or read out of the ASIC. The fifth control input is a two bit input "A0–A1" used to select any one of four available, predetermined control functions provided by the ASIC.

During System operation, the microprocessor interface responds to instructions and commands entered by the system operator on the laptop computer and generates the appropriate chip commands to cause the ASIC to carry out the desired function.

In the illustrated embodiment, basic switching between the various input and output pins of the ASIC is achieved as follows. First, the ASIC is enabled by setting CS=0. Next, the address of the desired input pin is written into the B-ADDR register. This is achieved by setting RD=0 and WR=1. The B-ADDR register is selected by applying a "00" control word to the control inputs A0–A1. The address of the selected input pin is applied to the data inputs D0–D7. The address thus specified is then written into the B-ADDR register.

The address of the desired output pin is written into the R-ADDR register in similar manner. To select the R-ADDR register, the control word "01" is applied to the control inputs A0–A1. The address of the desired output pin is applied to the data inputs D0–D7. In this case, the changed control word causes the data on the data inputs D0–D7 to be written into the R-ADDR register rather than the B-ADDR register. After thus receiving the specified addresses for a particular input pin and a particular output pin, the ASIC the enables the switches as needed to connect the specified input pin with the specified output pin. Various sets and subsets of input/output pin combinations can thus be specified and implemented by the ASIC by sequentially specifying the desired combinations to the ASIC in this manner.

Information is written into and out of the COUNTER register in similar manner. Such information can be written into the COUNTER register using the WRITE control input or can be read out of the register using the READ control command. Data transfer into or out of the COUNTER register is specified by applying the control word "10" to the control inputs A0–A1. The actual data to be written into or read out of the CONTROL register are communicated to and from the ASIC through the data inputs D0–D7.

Various additional control functions, such as testing for shorted or open electrodes, can be achieved by writing instructions into, and reading status information out of, the CONTROL/STATUS register. The CONTROL/STATUS register is accessed by applying the control word "11" to the control inputs A0–A1. Command words are written into the CONTROL/STATUS register through the data inputs D0–D7 by setting RD=0. Status words are read out of the CONTROL/STATUS register by setting WR=0.

The word(B-ADDR) is also used to select an identification voltage source. The word (R-ADDR) is also used to select a second input pin as needed for the open/short tests, a stimulator input, a short/open signal generator input or an expansion channel.

Pulse counter operation is controlled by applying the control word "10" to the control inputs A0–A1. An 8-bit command word can be written into the counter register (RD=0), or the count in the register can be written out of the register (WR=0) through the data inputs D0–D7. The available commands include count load/read back, enable/disable and up/down.

The detection of shorted and open electrodes can be performed either "exhaustively" or by specifying particular pairs. In the "exhaustive" test, all possible combinations of input and output pins are tested. Although effective in finding all potential malfunctions, such a test takes considerable time. Alternatively, the interface 32 can be operated so that tests for shorted conditions are performed only between specified pairs of inputs and outputs. Operating speed is considerably increased using such a test protocol. In the illustrated embodiment, selection between the "exhaustive" test and particular pair test is specified by setting selected bits of the status word to "1". For example, when D1=1 in the command word, the exhaustive test is performed. If D2=1 in the command word, then an open/short test is performed between two inputs defined by the B-ADDR and R-ADDR words.

The interface 32 preferably provides "command handshaking" to verify proper command receipt and execution. In the illustrated embodiment, appropriate control signals are generated in response to receipt of the various control commands and are reported back from the ASIC 58 to the microprocessor interface to verify proper command receipt and execution.

One example of available command and status-word formats preferably employed in the ASIC 58 is shown in the table of FIG. 14. As illustrated, each bit of the 8-bit command word has a particular significance. When that bit is set to "1", the desired control function is achieved. Alternatively, and as illustrated in FIG. 15, binary combinations of up to 4 bits can be used to signify the desired control function, and the remaining 4 bits of the command word can be used as a parity check to ensure proper receipt of the desired command. In the embodiment illustrated in FIG. 15, for example, bits D0–D3 of the command word specify in binary form the desired command, and bits D4–D7 the parity number. By comparing the parity numbers of the two, four-bit sets, proper command receipt can be verified.

FIG. 16 shows in tabular form one available format for the status word. As illustrated, each bit of the 8-bit status word represents a particular status of various blocks of the ASIC. For example, D0=1 indicates that the switch selected for polling is ON. D1=1 indicates the presence of short circuits between selected inputs. D2=1 similarly indicates open conditions.

Preferably, the computer 34 includes software that stores and executes various "protocols" that have been developed in advance. The protocols, in turn, are designed to define and implement various desired pacing and recording switching configurations. As previously noted, the precise switching configurations actually implemented by the various protocols are determined by such factors as the nature, number and locations of the various electrodes employed by a particular catheter, the type and configuration of biological recorder or other data acquisition system employed and the particular diagnostic or therapeutic procedure being performed. Because the ASIC 58 permits complete bidirectional interconnectivity among the various input pins, output pins and on-chip sub-systems, considerable operating flexibility is provided and is limited primarily only by the capabilities of the computer 34 and the software therein contained.

In one embodiment, the ASIC 58 can be implemented using known 40–100 V BiCMOS fabrication techniques. Preferably, a 2-micron feature size is employed. The IC package can be, for example, a QFP 240 (240 pin) or QFP 208 (208 pin) surface-mount plastic package. Alternatively, the ASIC 58 can be designed in a multi-die package. To ensure that electrograms are not distorted, the noise figure introduced by the ASIC 58 should be less than 30 $\mu$VRMS between 1 and 300 Hz. The impedance at frequencies below 2 KHz. when any switch is "ON" is preferably less than 200 $\Omega$ at higher input voltages. The impedance below 2 KHz. when any switch is "OFF" is preferably greater than 500 k$\Omega$. The insertion attenuation of pacing current directed to an individual catheter electrode is preferably better than −0.1 dB. The low identification voltage is preferably 1 mV while the high identification voltage is preferably 10 mV. It will be appreciated that, although these specified operating parameters and specifications are preferred for the application and in the embodiment herein described, other operating parameters and design specifications can be used. It will also be appreciated that other numbers of input pins, output pins, external source inputs etc. can be used beyond those shown and described.

The interface system 11 as shown and described herein is particularly well suited for certain applications. For example, it is sometimes desirable to apply pacing pulses to the heart and then record the resulting cardiac signals using the same set of electrodes. However, because the pacing pulse amplitude greatly exceeds the amplitude of the resulting cardiac signals, an biological recorder directly coupled to the electrodes is driven into saturation by the applied pacing pulses. The biological recorder is thus rendered incapable of recording the resulting cardiac signals until recover from saturation. Cardiac signal data occurring during the recovery period is lost.

The interface system 11 permits more thorough and accurate recovery of cardiac signals in the period immediately following the application of a pacing pulse. To this end, the ASIC 58 can be operated to disconnect the inputs to the biological recorder from the electrodes during the period in which a pacing pulse is applied and to reconnect the electrodes to the biological recorder inputs immediately following application of the pacing pulse. Referring to FIG. 5, the edge detector 64 detects the edges of the applied pacing pulses. The control circuitry 70, by monitoring the occurrence of each applied pacing pulse, can, after a small number of pulses have been applied, then determine the pulse duration as well as the pulse application frequency. With such information, the control circuitry 70 can then actuate the ASIC 58 to temporarily disconnect the electrodes 16 from the inputs to the biological recorder 30 during the period in which the pacing pulse is applied and reconnect the electrodes immediately after the applied pacing pulse terminates. By so disconnecting the electrodes 16, the input channels of the biological recorder are never driven into saturation an the biological recorder input channels are immediately ready to record the cardiac signals induced by the applied pacing pulse. Alternatively, the derivative of the pacing pulse can be used to detect the leading and trailing edges of the pacing pulse. Based on this information, the control circuitry 70 can then actuate the ASIC 58 to temporarily disconnect the electrodes 16 when the leading pulse of the pacing pulse occurs and reconnect them immediately after the trailing edge has been detected.

Similarly, adaptive filtering can be used to remove pacing overvoltages and thereby avoid saturation of the biological recorder. Adaptive filtering blocks can be used as functional blocks of the ASIC 58. Suitable adaptive filtering techniques are shown, for example, in the co-pending application Ser. No. 08/390,559 filed Feb. 17, 1995, now abandoned the specification of which is incorporated by reference herein.

It will be appreciated that use of the switching transistor arrangements herein shown and described enable the ASIC to pass the relatively low lever cardiac signals sensed by the electrodes 16 while enabling the ASIC to resist without damage the much higher amplitudes of the applied pacing pulses.

The Graphical User Interface (GUI)

The interface system 11 further includes a Graphical User Interface (GUI) that is implemented on, and resident in, the computer 34. The GUI functions to provide the attending medical personnel with a pictorial or graphic representation of the multielectrode catheter 14 within the patient's body. The various individual electrodes 16 and roving electrode 19 are indicated, as are their locations and orientations relative to themselves. The representation of the multielectrode catheter 14 and/or roving electrode 19 may be manipulated on the display screen 38 until it suggests the orientation of the catheter 14 within the patient's body 12. The orientation may be guided and confirmed by comparing the appearance of the representation of the catheter 14 to the appearance of the catheter on the fluoroscope display 28. Such display helps "orient" the attending personnel with respect to the catheter 14 and the patient's body 12 and thus helps them interpret the data provided by the catheter 14.

The display of the position of the roving electrode 19 helps the physician in guiding diagnosis or therapy application.

The GUI makes use of the human ability to process information more readily when presented in a graphic form than when presented as a series of numerical data points. The graphic model of the multielectrode catheter 14 within the body 12 that the GUI provides enables the attending personnel to visualize the locations of the individual electrodes 16 in relation to actual tissue and thus helps the personnel interpret the data obtained by each electrode 16. The GUI further enables the personnel to "turn" their point of view relative to the catheter 14 and the patient 12 and thus "see" the catheter 14 from positions that are not physically realizable. For example, the Inferior view displays the multiple electrode structure as seen by a viewer looking horizontally from the patient's feet. The Superior view displays the multiple electrode structure as seen by a viewer looking horizontally from the patient's head. The Left or Right 90 views are views orthogonal to the main views AP, RAO or LAO, depending on which view has been selected for display in the left half-screen. For example, if the left half-screen displays a LAO 30 view, Right 90 would be the corresponding orthogonal view and equivalent to RAO 60. Similarly, Left 90 would correspond to LAO 120, although this angle is not physically realizable. Some fluoroscopes include a pair of heads and sensors oriented at right angles to each other. The GUI also enables the personnel to label various electrodes 16, enter notes onto the display 38 and otherwise add visual or informational prompts or cues that further aid in interpreting the information provided by the catheter 14.

The GUI provides a graphical model that represents how a catheter 14 would be situated relative to various anatomical structures if certain assumptions concerning the catheters' location are correct. By reference to this model, the attending personnel are able to visualize were each electrode 16 and spline 18 is located within the patient's body 12.

During a diagnostic or other medical procedure, the fluoroscope 22 is used to monitor the position of the catheter 14. The GUI provides a simplified and idealized representation that supplements the fluoroscopic image 28.

Figure 17:
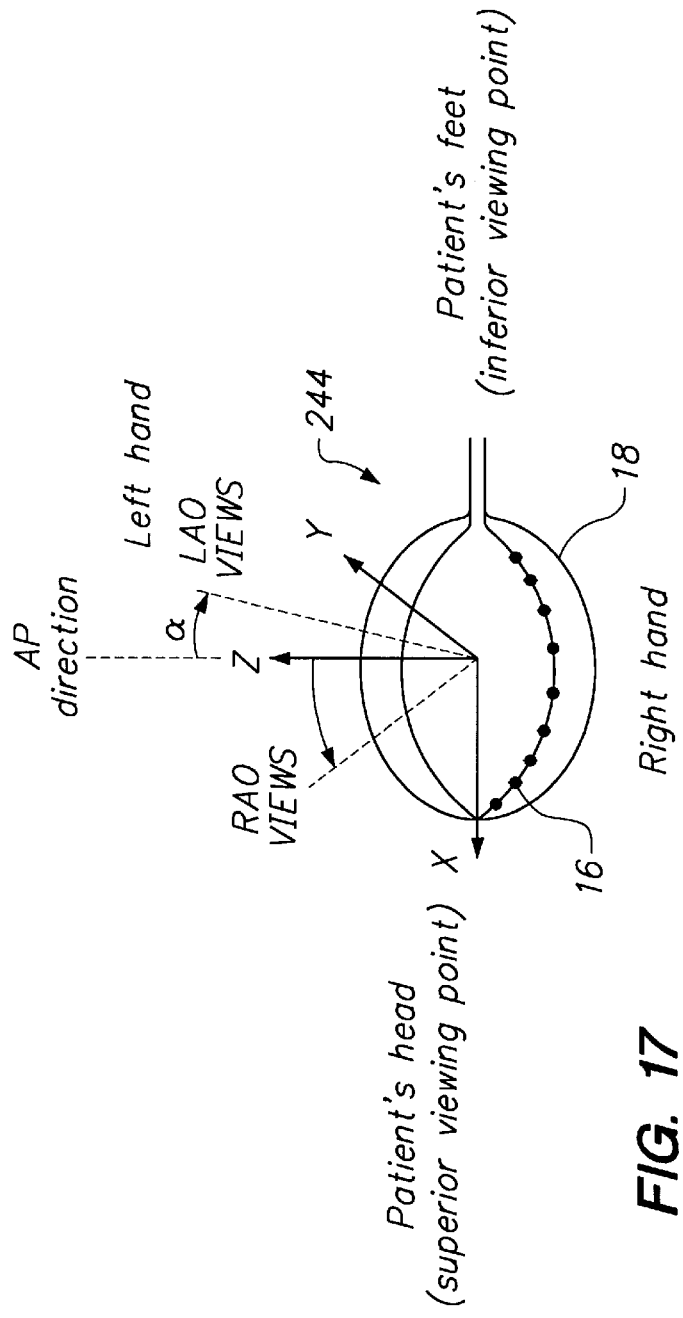
FIG. 17 is a diagrammatic representation of a multiple electrode catheter and a system of coordinates useful in describing positions relative to the multiple electrode catheter.

Certain fluoro angles are more frequently used in the field of fluoroscopy. FIG. 17 illustrates the viewing angles for such views, with respect to the coordinate system associated to the wire-frame representation of the multiple electrode structure. These views are: Right-Anterior-Oblique (RAO) 30 or 45, Anterior-Posterior (AP) and Left-Anterior-Oblique (LAO) 30 or 45. The AP View is provided when image intensifier 26 is positioned perpendicular to the patient's chest. The LAO view is provided when the image intensifier 26 is positioned over the left side of the patient's chest. The RAO view is provided when the image intensifier 26 is positioned over the right side of the patient's chest. The angle with respect to the AP orientation is attached as a suffix to the LAO or RAO nomenclature (e.g. if the angle is 30 degrees the view is labeled RAO30 or LAO30). The simultaneous orthogonal views presented by such fluoroscopes further assist the physician in following the progress of the catheter into the patient's body.

When placed into operation, the GUI displays a simplified, idealized graphical image of the particular type of multielectrode catheter 14 being used in the procedure. In the illustrated and preferred embodiment, the GUI provides a split screen image having a left panel 240 and a right panel 242 (FIG. 1). A wire-frame image 244 of the catheter 14 appears in standard orientations on both the right and left panels. The particular GUI shown and described is intended for use with a single type of multielectrode catheter 14 of the type shown and described in U.S. Pat. No. 5,549,108 issued Aug. 27, 1996 entitled "Cardiac Mapping and Ablation Systems" and U.S. Pat. No. 5,509,419 issued Apr. 23, 1996 entitled "Cardiac Mapping and Ablation Systems" and commonly owned by the assignee hereof. Accordingly, information regarding the catheter is already retained within the GUI. Alternatively, in other embodiments, the system operators can enter the type of catheter that is being used. The GUI can then display the type of catheter thus selected.

After the initial form of the catheter 14 is displayed, it is necessary next, to set the view in the left panel 240 to match the view of the fluoroscope 28. To this end, the attending personnel compares the fluoroscopic image 28 of the catheter 14 and then manipulates the GUI image 244 on the left panel 240 so that the catheter 14 shown thereon closely matches the live view as seen on the fluoroscopic display 28. To accomplish this, the GUI includes a plurality of on-screen buttons 246 (FIG. 3) that can be pressed to cause the catheter image 244 to rotate. These buttons are the X, Y and Z orientation buttons. These buttons are used to change the relative position of the multiple electrode catheter orientation from its initial position. Thus, the system operator moves the cursor to one of the orientation buttons and presses the left mouse button. This action causes the catheter image 244 to rotate about an idealized coordinate axis 48 located at the virtual multiple electrode catheter center shown in FIG. 17. As to be expected, the X orientation button rotates the multiple electrode catheter image 244 in either a left-to-right or right-to-left direction, the Y orientation button rotates the multiple electrode catheter image in either a top-to-bottom or bottom-to-top direction and the Z orientation button rotates the multiple electrode catheter image in either a clockwise or counterclockwise direction.

Assume a point $P_0$ of coordinates $x_0$, $y_0$, $z_0$ on the envelope surface of the structure 14. After a rotation of angle $\alpha$ about the X axis the new position of $P(x, y, z)$ is given by equation (1).

$$\begin{bmatrix} x \\ y \\ z \end{bmatrix} = \begin{bmatrix} 1 & 0 & 0 \\ 0 & \cos(\alpha) & \sin(\alpha) \\ 0 & -\sin(\alpha) & \cos(\alpha) \end{bmatrix} \cdot \begin{bmatrix} x_0 \\ y_0 \\ z_0 \end{bmatrix}$$

Equation (2) and (3) define rotations of angle $\alpha$ about the Y and Z axis, respectively:

$$\begin{bmatrix} x \\ y \\ z \end{bmatrix} = \begin{bmatrix} \cos(\alpha) & 0 & \sin(\alpha) \\ 0 & 1 & 0 \\ -\sin(\alpha) & 0 & \cos(\alpha) \end{bmatrix} \cdot \begin{bmatrix} x_0 \\ y_0 \\ z_0 \end{bmatrix}$$

$$\begin{bmatrix} x \\ y \\ z \end{bmatrix} = \begin{bmatrix} \cos(\alpha) & \sin(\alpha) & 0 \\ -\sin(\alpha) & \cos(\alpha) & 0 \\ 0 & 0 & 1 \end{bmatrix} \cdot \begin{bmatrix} x_0 \\ y_0 \\ z_0 \end{bmatrix}$$

In general, if a sequence of X, Y, or Z rotations is performed, the final coordinates of the point P depend on the exact order the rotations are performed in.

Figure 18A:
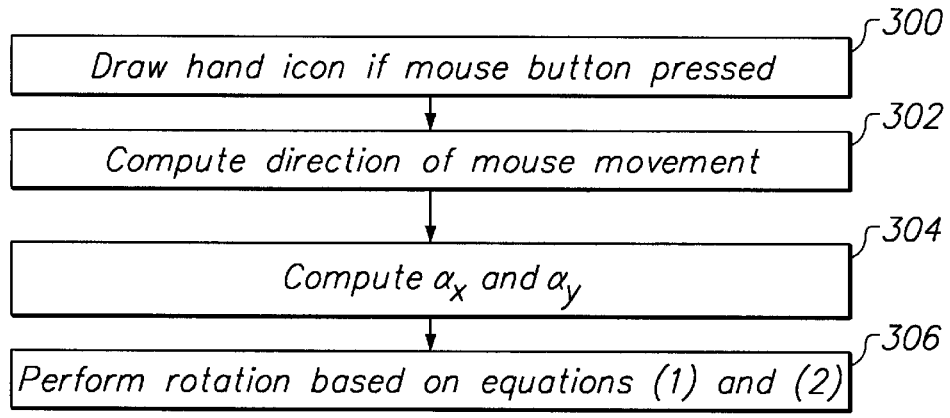
FIG. 18(a) is a flowchart diagram useful in understanding an algorithm used to rotate a wire-frame display of a multiple electrode structure using a mouse.

Alternatively, the system operator may utilize the mouse controls to rotate the multiple electrode catheter image. Whenever the cursor is positioned in the left panel 240 and the left mouse button is pressed, the cursor changes from an arrow-style image to that of a hand-style image 250. This action causes the movement, that is to say, the rotation of the multiple electrode catheter image in response to the movement of the mouse by the system operator. By keeping the mouse left button pressed, the system operator may position the multiple electrode catheter image. When the left mouse button is released, the multiple electrode catheter image 244 remains in the current orientation. FIG. 18(a) presents the flowchart of the algorithm for the mouse-driven rotation. Element 300 draws the hand icon when the mouse button is pressed. Element 302 computes the direction of mouse movement. Based on this information, element 304 computes two rotation angles about the X and Y axes. Element 306 performs the actual rotation based on equations (1) and (2) above. The action of rotating the wire-frame multiple electrode catheter representation 244 in the left panel 240 by means of X, Y and Z orientation button or mouse movement may be repeated until the system operator is satisfied with the orientation of the multiple electrode catheter image in reference to the fluoroscopic image 28.

Preferably, the wire-frame representation 244 of the multiple electrode catheter 14 shows a plurality of splines 252 corresponding in number to the actual number of splines 18 used in the multielectrode catheter 14 and further shows a plurality of electrodes 254 on each spline 252 corresponding in number to the actual number of electrodes 16 on each spline 18. In the preferred embodiment, splines 252 and electrodes 254 on the wire-frame image 244 are highlighted, colored differently, sized distinctly or otherwise distinguished visually from the others to provide a representation of the multiple electrode catheter in a virtual three-dimensional space where the center of the wire-frame model 244 is designated as the center of that three-dimensional space. In the illustrated embodiment, the wire-frame image 244 is generated such that splines 252 and electrodes 254 which lie in the background of the three-dimensional space (i.e., behind the center of the three-dimensional space as viewed from the system operator's viewing angle) appear darker or shadowed compared to the splines 252 and electrodes 254 appearing in the foreground. This enhances the three-dimensional appearance of the multiple electrode catheter image 244 on the screen 38.

Once the orientation of the virtual multiple electrode catheter image is matched to the real fluoroscopic image, as viewed by the system operator, it may be saved or stored in the computer memory by pressing the "Save View" button. The "Save View" button provides for the system operator to save or store the current multiple electrode catheter image as any of the standard views, i.e., the "AP", "LAO45", "LAO30", "RAO30" OR "RAO45" views.

To further assist the operating personnel in interpreting what they see, it is frequently helpful to provide other viewing angles that are related to the standard fluoroscopic view but not realizable by such equipment. To this end, the GUI based on the properly orientated image shown in the left panel of the display, is operable to generate and display multiple electrode catheter images in the right panel that are orthogonal to the view in the left panel. Such orthogonal views are displayed in the right panel relative to the view set in the left panel.

In the illustrated embodiment, the GUI provides orthogonal views calculated from the "Superior", "Inferior", "Left 90" and "Right 90" views.

Preferably, the wire-frame representation 244 of the multiple electrode catheter 14 shows a plurality of splines 252 corresponding in number to the actual number of splines 18 used in the multielectrode catheter 14 and further shows a plurality of electrodes 254 on each spline 252 corresponding in number to the actual number of electrodes 16 on each spline 18. Preferably, one or more of the splines 252 or electrodes 254 is highlighted or otherwise distinguished visually from the others to provide a reference for orienting the displayed wire-frame image 244. In the actual catheter 14, one or more of the splines 18 or electrodes 16 are provided with a fluoroscopic marker that appears on the fluoroscope screen 28 and that serves to identify a particular one of the electrodes 16 for reference purposes. The electrode 260 highlighted by the GUI corresponds to this electrode and is positioned to closely match the position of the corresponding electrode on the fluoroscope screen 28.

The described procedure thus coordinates the "three dimensional" wire-frame multiple electrode catheter representation 244 generated and displayed by the GUI with the two dimensional display of the actual multiple electrode catheter 14 shown on the fluoroscope screen 28.

After the displayed multiple electrode catheter image 244 is properly oriented, the view can be saved by clicking the "Save View" and "OK" buttons that appear on the display screen 38.

In the illustrated embodiment, the wire-frame image 244 generated on the left panel 240 of the display 38 corresponds to the view of the multiple electrode catheter 14 displayed on the fluoroscope screen 28. To further assist the operating personnel in interpreting what they see, it is frequently helpful to provide other views that are not easily realizable using the fluoroscopic equipment 22. To this end, the GUI, based on the properly oriented image 244 shown on the left panel 240 of the display 38, is operable to generate and display images 244' of how the multiple electrode catheter image 244 would appear if view from other angles. Such alternate views are displayed on the right panel 242 of the display 38.

In the illustrated embodiment, the GUI provides "Superior," "Inferior," "Left 90°" and "Right 90°" views. These views are obtained by clicking the appropriately labeled corresponding buttons on the screen 38. The image appearing on the right panel 242 of the display 38 tracks the orientation of the image 244 on the left panel 240. Thus, if the image orientation on the left display panel 240 is changed or adjusted, the right image 244' will also change to reflect the new orientation of the catheter 14 relative to the body.

In the illustrated embodiment, fluoro angles between −90° and +90° can be used and can be entered into the GUI. Thus, the GUI can be still be effectively used if, for some reason, the attending personnel elect to position the fluoroscope to a non-standard fluoro angle. In the illustrated embodiment, views at the standard fluoro angles of −45°, −30°, 0°, +30° and +45° can be automatically saved. Customized views at non-standard fluoro angles can also be named and saved.

As previously mentioned, the primary function of the GUI is to provide a visual image or model 244 that assists the operating personnel in visualizing the multiple electrode catheter 14 within the patient's body 12 and interpreting the data acquired from the multiple electrode catheter 14. Although this is largely achieved by orienting the wire-frame display representation of the electrode basket to match the actual image provided by the fluoroscope, the GUI provides several additional functions that further enhance its effectiveness. Various of these additional functions are described below.

A MARKERS function is provided which enables the operator to alter and enhance the displayed multiple electrode catheter wire frame image. The MARKERS function includes an ADD MARKER function that enables the operator to add an identifier or marker to selected locations of the electrode image 244 displayed in the left screen 40. This function is useful if the operator wishes to mark selected locations that are significant or of interest, such as mapping sites, ablation sites, etc. By having such sites highlighted or otherwise distinguished, the operator is better able to remain coordinated and oriented with the displayed image and, therefore, better able to interpret data recovered by the multiple electrode structure. The markers appear on the surface defined by the various splines 252.

Figure 18B:
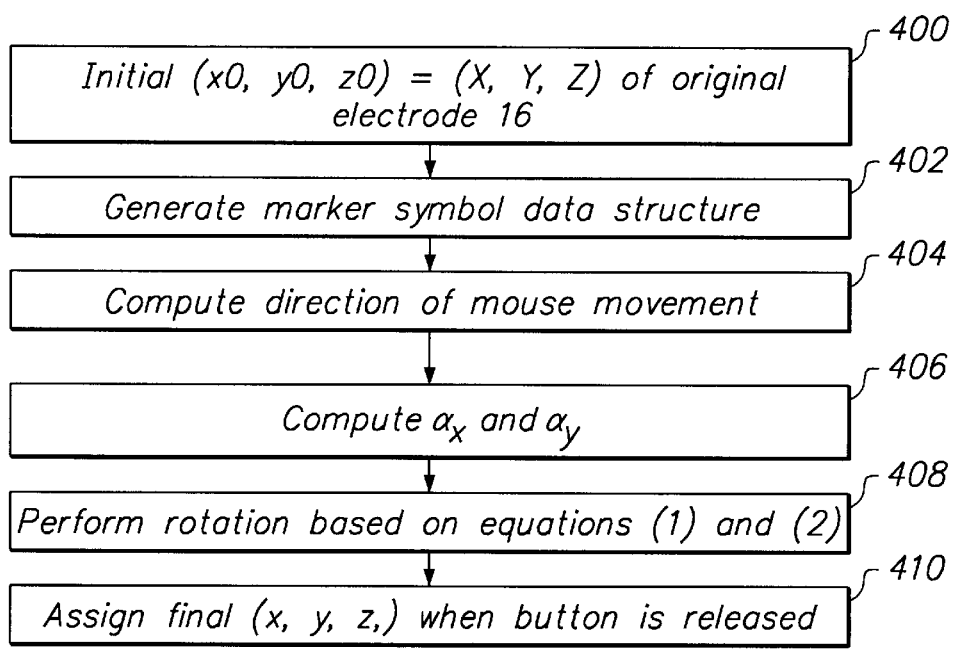
FIG. 18(b) is a flowchart diagram useful in understanding the operation of an algorithm used to identify user-requested electrodes within the wire-frame display of the multiple electrode structure.

The MARKERS function is used by clicking the ADD MARKER button that appears on the screen after the general "MARKERS" button is clicked. Pressing the right mouse button on an electrode causes a marker to appear on the screen. With the right button thus depressed, the mouse is used to "drag" the marker over the implied surface of the multiple electrode catheter to the desired location. When the right button is released, the marker is "dropped" into the desired marker location. Markers can thus be placed near electrodes on either the foreground or background of the multiple electrode catheter. FIG. 18(b) shows the flowchart of the algorithm used to add markers. Element 400 assigns the initial $x_0$, $y_0$, $z_0$ coordinates of the marker when the mouse button is pressed. These initial coordinates are identical to those of the electrode 16 acting as origin of the placement. Element 402 generates the marker symbol and inserts the corresponding software data structure into a linked list. Element 404 computes the direction of the mouse movement based on information received from the mouse port. Element 406 converts the direction information into two rotation angles, about the X and Y axes, respectively. Element 408 computes the new location of the marker based on equations (1) and (2). Element 410 assigns the final x, y, z coordinates to the marker when the mouse button is released. Markers are created as data structures comprising: pointer to previous marker, order number, coordinates, comments, time stamp and pointer to next marker.

Also included in the MARKERS function is a COMMENT function that enables the operator to add custom notes or comments to each marker. For example, if the operator wishes to comment on the significance of each selected, marked site, the COMMENT function can be used for this purpose. A COMMENT window appears as soon as the marker is "dropped" at the selected site. A time stamp is preferably included in the comment. The operator can enter the desired comment into the comment window using the computer keyboard. By clicking the OK button, the comment thus entered is saved. If no comment is desired, the CANCEL button can be clicked. A PREV. COMMENT button is provided which, when actuated, displays comments previously entered with earlier markers. A NEXT COMMENT button displays comments associated with later entered markers. Once a marker is "dropped," its comments can be retrieved by placing the cursor onto the marker and pressing the right mouse button.

A DELETE MARKER function is provided for deleting previously entered markers. This function is actuated by clicking on the DELETE MARKER button and thereafter placing the cursor on the desired marker. When the right mouse button is pressed, the selected marker is deleted. When a DELETE operation is performed the corresponding marker data structure is removed from the linked list by employing well-known data structure software techniques.

The MARKERS function is terminated by clicking the CLOSE button.

The GUI also provides a mapping function that enables the operator to create any of five types of binary maps. The available mapping functions are (1) EARLY ACTIVATION, (2) FRACTIONATION, (3) GOOD PACE MAP, (4) CONCEALED ENTRAINMENT and (5) USER DEFINED and are characterized as follows:

EARLY ACTIVATION. The EARLY ACTIVATION mapping function identifies and marks the electrodes where early depolarization of the heart tissue has occurred. Early depolarization is often an indicator of abnormal heart tissue adjacent the electrode.

FRACTIONATION. The FRACTIONATION mapping function identifies and marks the electrodes where the electrograms sensed by such electrodes appear fractionated or broken in appearance. Again, the existence of fractionated electrograms a particular electrode site is often an indicator of abnormal cardiac tissue at that site.

GOOD PACE MAP. The GOOD PACE MAP mapping function identifies and marks the electrodes with high pace mapping matching index. This index reflects how many of the morphologies of 12-lead surface electrocardiograms (ECG) acquired during non-induced arrhythmia match the morphologies of the same signals acquired during paced induced arrhythmia from the particular electrode. If by pacing from a particular electrode 16, a high number of the 12-lead ECG morphologies are similar during non-induced and pace-induced arrhythmia then it is likely that the particular electrode 16 resides close to an arrhythmogenic focus.

CONCEALED ENTRAINMENT. The CONCEALED ENTRAINMENT mapping function identifies and marks the electrodes where arrhythmia entrainment was achieved. Abnormal cardiac tissue often is located electrodes exhibiting CONCEALED ENTRAINMENT.

USER DEFINED. The USER DEFINED mapping function enables the user to specify particular criteria to be used for categorizing signals obtained by the multiple electrodes. Electrodes providing signals meeting the selected criteria are identified and marked. The USER DEFINED mapping function allows the physician to locate areas of cardiac tissue exhibiting certain preselected characteristics and further enhances the diagnostic function of the system.

The various mapping functions are of importance in identifying potential ablation sites. Frequently, abnormal cardiac tissue, which can be effectively treated through ablation, often exhibits more than one abnormal characteristic. Such sites frequently appear on two or more of the EARLY ACTIVATION, FRACTIONATION and CONCEALED ENTRAINMENT maps. If the same electrode or groups of electrodes appear on two or more of the ACTIVATION, FRACTIONATION, GOOD PACE MAP and CONCEALED ENTRAINMENT maps, a likely site for ablation is particularly well indicated.

Numeric values, such as activation time numbers, cardiac signal voltages, or propagation velocities, can be associated to each electrode of the multielectrode catheter structure. Then, isovalues (i.e., isochronal, isopotential, isoconduction etc.) can be generated. The isovalue maps can be used in association with the binary maps, markers and anatomic features to further identify potential ablation sites.

The mapping function is initiated by clicking the CREATE MAP button that appears on the display screen. When this button is clicked, a pop-up window appears offering a choice of any of the five mapping functions. By clicking on the selected choice, the desired mapping function is initiated.

After the desired mapping function is selected, the mouse is used to drop binary map markers at the electrodes of interest. This is done by moving the mouse to place the cursor over the electrode of interest and then depressing the right mouse button to drop the marker at the selected electrode. The algorithm for generating binary map markers is substantially similar to that shown in FIG. 18($b$). The only difference is that the rotation step 408 is not performed. The binary map markers are directly attached to the selected electrode 16. Similar data structure techniques are used to create and update the required binary map linked lists. The data structure corresponding to a binary map marker comprises: pointer to previous marker, electrode number, binary map type, comment, time stamp, isovalue type and pointer to next marker. After the selected electrodes are thus marked, a different type of binary map can be selected or the CLOSE button appearing on the pop-up window can be clicked. Specific comments can be entered by the operator using the computer keyboard. If the comments are acceptable, the OK button is then clicked. If not, the CANCEL button is clicked and the comments are not saved. Comments can later be retrieved by placing the cursor over a binary map marker and then pressing the right mouse button.

Various other functions are provided in connection with the mapping function. A SHOW MAP function can be selected by clicking the SHOW MAP button. This function displays the types of binary maps that are available. By clicking on one of the listed types, the selected binary map will then be displayed. The types of maps being displayed will be indicated with a check mark (✓).

A CLEAR MAPS button functions, when clicked, to delete and clear all existing binary maps.

A REMOVE MAP POINTS button operates, when clicked, to clear a specific map point by placing the cursor on the map point to be removed and clicking the right mouse button.

A CLOSE button functions, when clicked, to close the BINARY MAP function.

Still additional functions are provided by the GUI.

A FEATURES function displays a pop-up window with choices for anatomic markers. The anatomic markers function to indicate on the display the location of certain anatomic structures or landmarks (e.g., the aortic valve, the inferior vena cava, the superior vena cava etc.) relative to the multiple electrode catheter. Having the relative locations of such anatomical structures displayed relative to the multiple electrode catheter and its other features helps the physician in guiding the catheter, and in mapping and treating the cardiac tissue.

To operate this function, the FEATURES button is clicked, which causes a pop-up window to be displayed. The window displays a number of choices for anatomic markers. The desired anatomic marker is selected using the cursor, and the marker is then dragged to the desired location using the right button of the mouse. At the desired location, the right mouse button is released to drop the marker at the desired location. The algorithm which inserts these anatomic markers works similarly to that shown in FIG. 18($b$). However, the anatomic markers are not created as linked lists data structures. The anatomic markers can be deleted as a group by clicking on the CLEAR ALL FEATURES button, or can be selectively deleted by clicking the REMOVE FEATURE button.

A PRINT function can be selected by clicking on the PRINT button. This function prints both multiple electrode catheter views plus current and existing comments on the system's default printer.

A SAVE VIEW function saves the selected principal view (i.e., the left screen panel) when actuated. All other views are updated accordingly.

A SHOW SPLINES function labels the individual splines of the electrode basket when actuated. This button also turns into HIDE SPLINES to facilitate label removal when desired. Spline labels in the foreground appear brighter than spline labels in the background to further enhance the three-dimensional effect provided by the GUI.

Figure 18C:
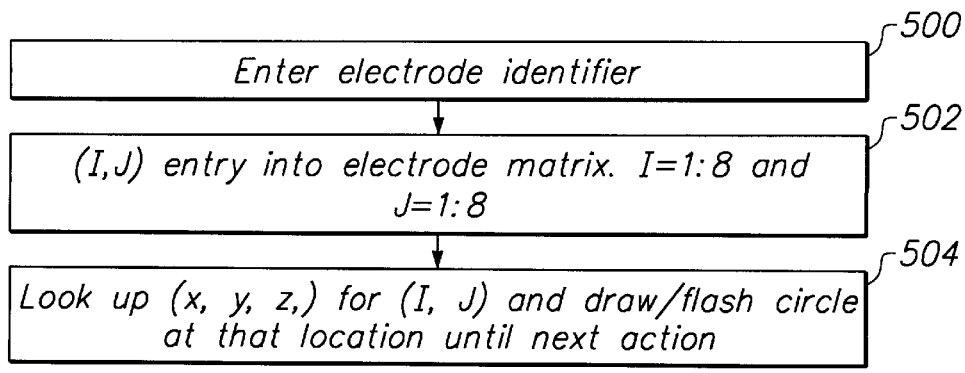
FIG. 18(c) is a flowchart diagram useful in understanding the operation of an algorithm used to associate markers or anatomical features with the wire-frame display of the multiple electrode structure.
Figure 19:
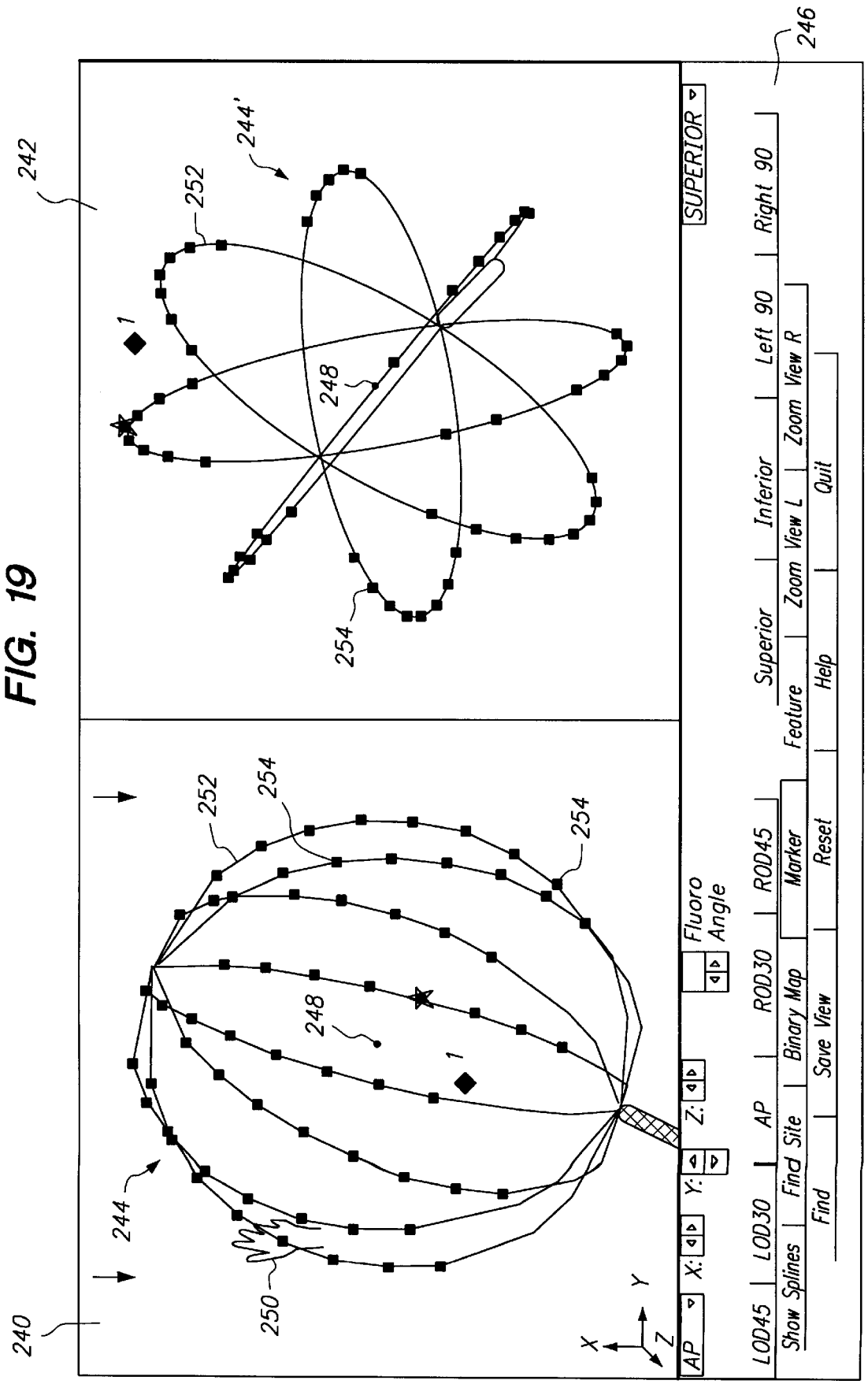
FIG. 19 is a sample of a display screen generated by the GUI, useful in understanding the look and feel thereof.

A FIND SITE function operates, when actuated, to enable the operator quickly to locate a particular electrode. When this function is actuated, the operator enters the designated electrode onto the keyboard and the GUI then highlights the electrode thus selected. In the illustrated embodiment, a circle is flashed around the selected electrode until a next action is taken. FIG. 18(c) illustrates the flowchart of the algorithm that implements the Find Site function. Element 500 accepts a user-entered electrode number (e.g. A4, D3) and returns an entry to a 8×8 matrix associated to the electrodes 16 on structure 14. Element 502 accepts as input the matrix entry and returns the x, y, z coordinates of the user-selected electrode 16. Element 504 draws and flashes a circle around the x, y, z coordinates received from element 302. Element 504 also checks whether any other action is issued by the computer 34. If the answer is yes then it stops the Find Site function and returns to normal screen.

A ZOOM VIEW L function operates, when actuated, to expand the left half-screen to a full screen view.

A ZOOM VIEW R function operates, when actuated, to expand the right half-screen to a full screen view.

A RESET function operates to reset the screen to a default view when actuated.

Various examples of the GUI in use are shown in FIGS. 20, 21, 22 and 23.

Figure 20:
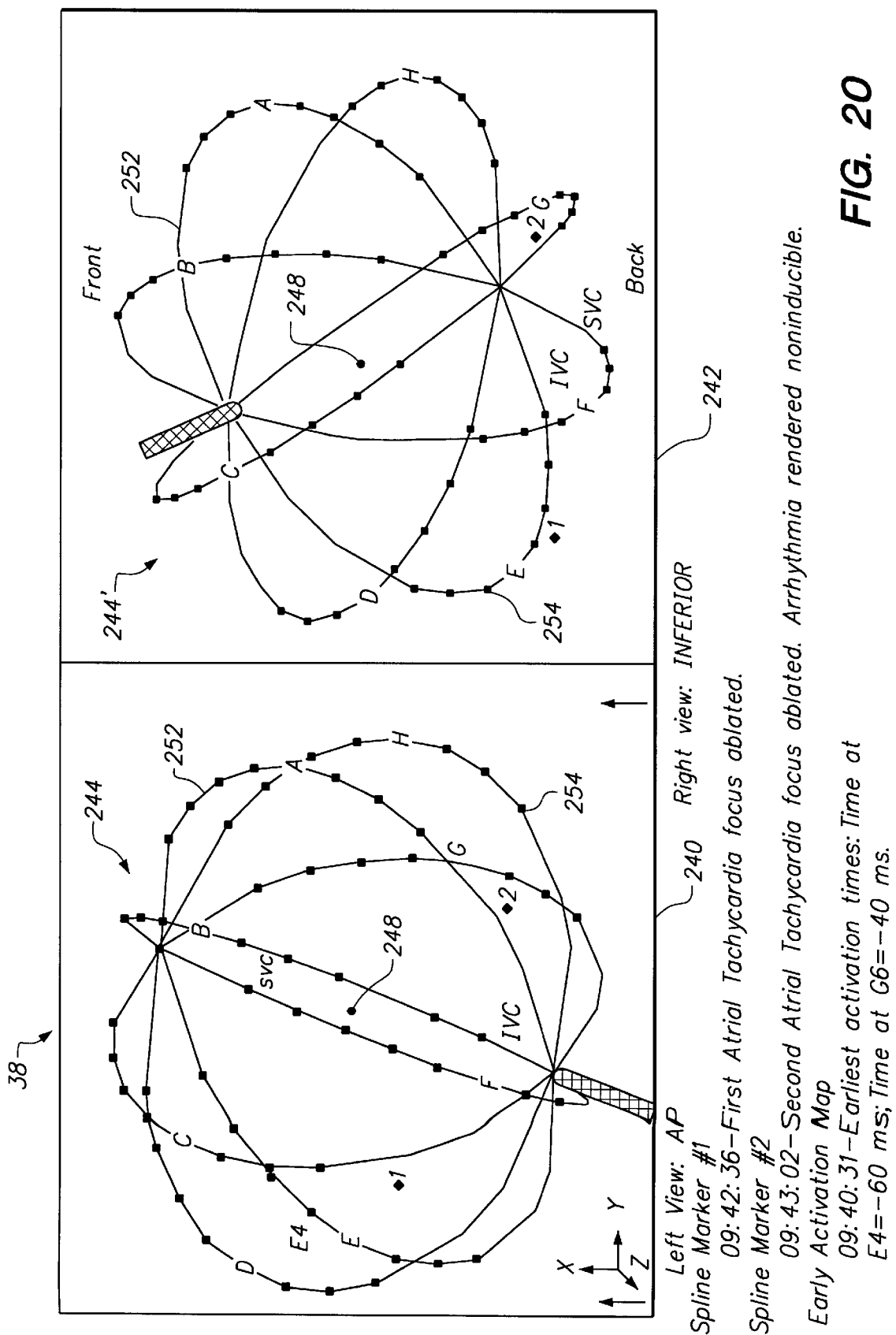
FIG. 20 is a sample of a display screen generated by the GUI showing a multiple electrode structure within the right atrium of a heart for purposes of diagnosing and treating atrial tachycardia within the right atrium.

FIG. 20 represents the multiple electrode structure within the right atrium of the heart. Display panel 240 shows the wire frame image 244 from the AP view, while the right panel 242 shows the image 244' from the inferior view. The relative locations of the Superior Vena Cava and Inferior Vena Cava are marked "SVC" and "IVC" respectively on the displays. A first early activation site is indicated by the marker ♦1, while a second early activation site is indicated by the marker ♦2. The user-entered legend under the display indicates that the first site was ablated at time 09:42:36, while the second site was ablated at time 09:43:02. The legend further indicates that the detected arrhythmia was rendered noninducible following such ablation, thereby indicating a successful treatment.

Figure 21:
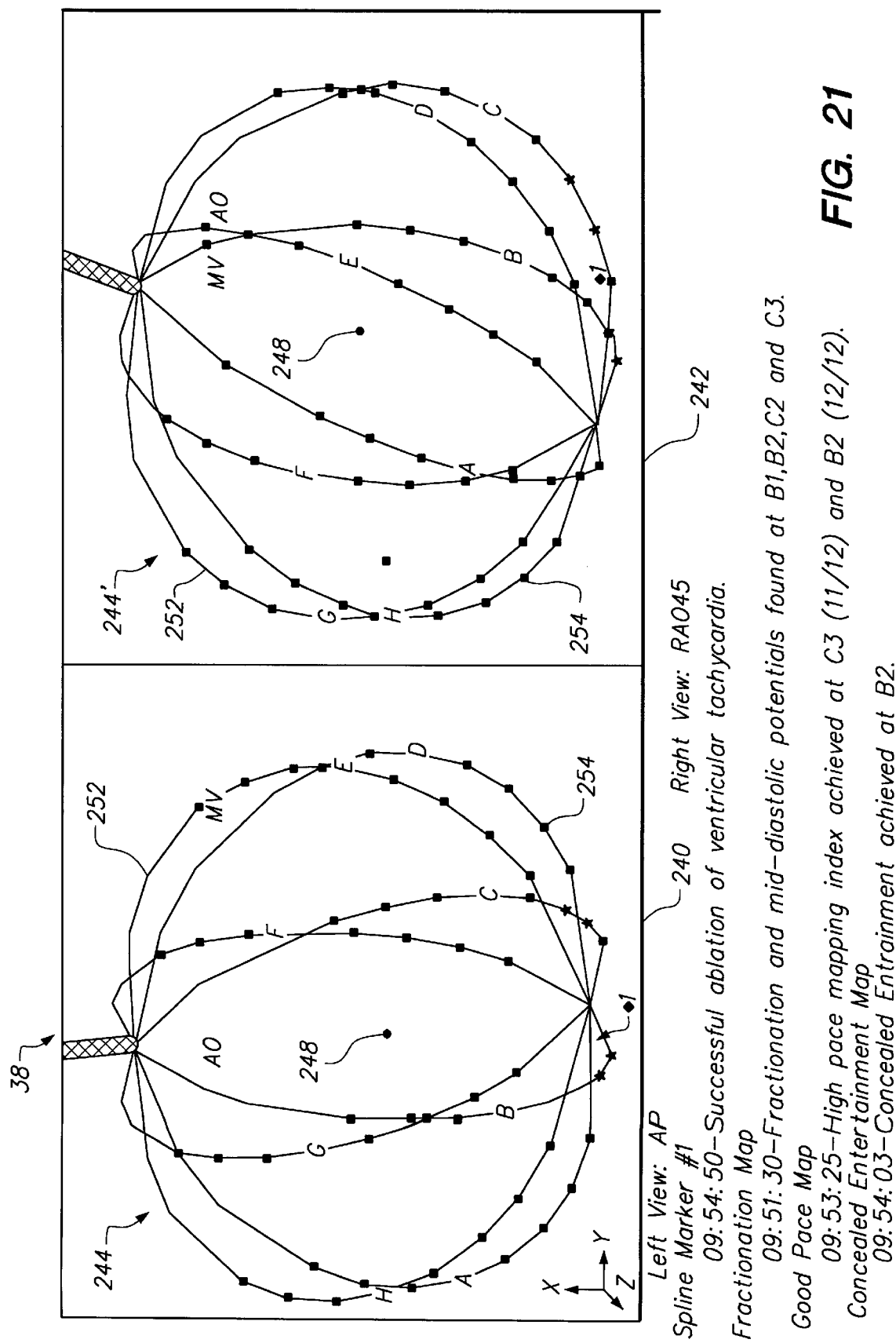
FIG. 21 is a sample of a display screen generated by the GUI showing a multiple electrode structure within the left ventricle of a heart for purposes of diagnosing and treating ventricular tachycardia within the left ventricle.

FIG. 21 represents the multiple electrode structure within the left ventricle for treatment of left ventricular tachycardia. In FIG. 21, the view in the left display panel 240 is from the AP position, while the view in the right panel 242 is from the RAO 45 position. In this example, the various binary mapping functions have ben used, and two sites satisfying two or more of the selection criteria have been located and indicated by the symbols ♦, ●, and ★. In particular, two sites exhibiting fractionation and concealed entrainment have been located and identified. Such sites are likely candidates for tissue ablation.

Figure 22:
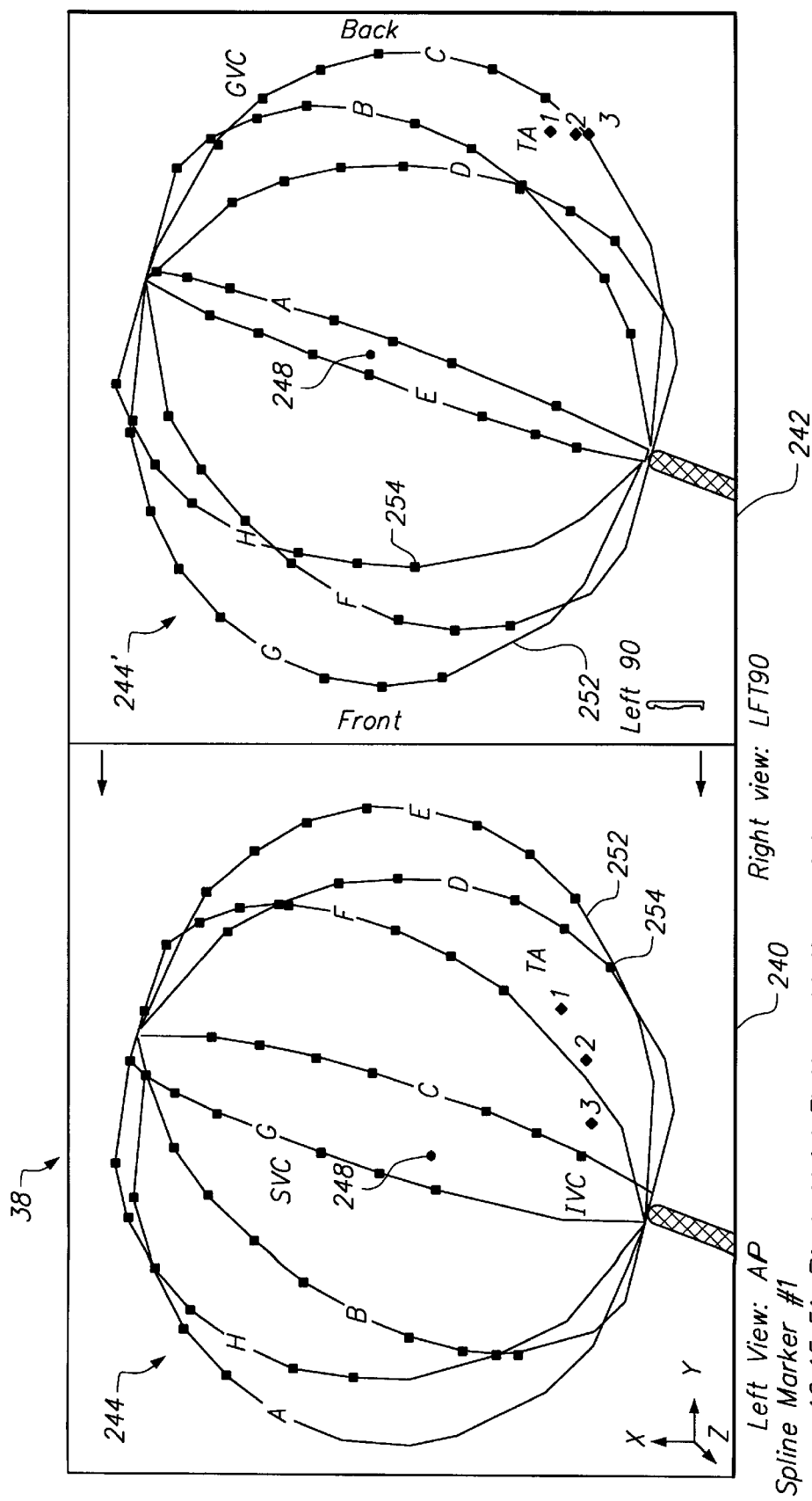
FIG. 22 is a sample of a display screen generated by the GUI showing a multiple electrode structure within the right atrium of a heart for purposes of diagnosing and treating atrial flutter within the right atrium.

FIG. 22 represents the multiple electrode structure within the right atrium for treatment of atrial flutter. The view in the left panel 240 is from the AP position, while the view in the right panel is from the LFT 90 position. Three markers, ♦1,♦2, and ♦3 are shown in both views. According to the user-entered legend, these markers indicate first, second and third atrial flutter ablation points, respectively.

Figure 23:
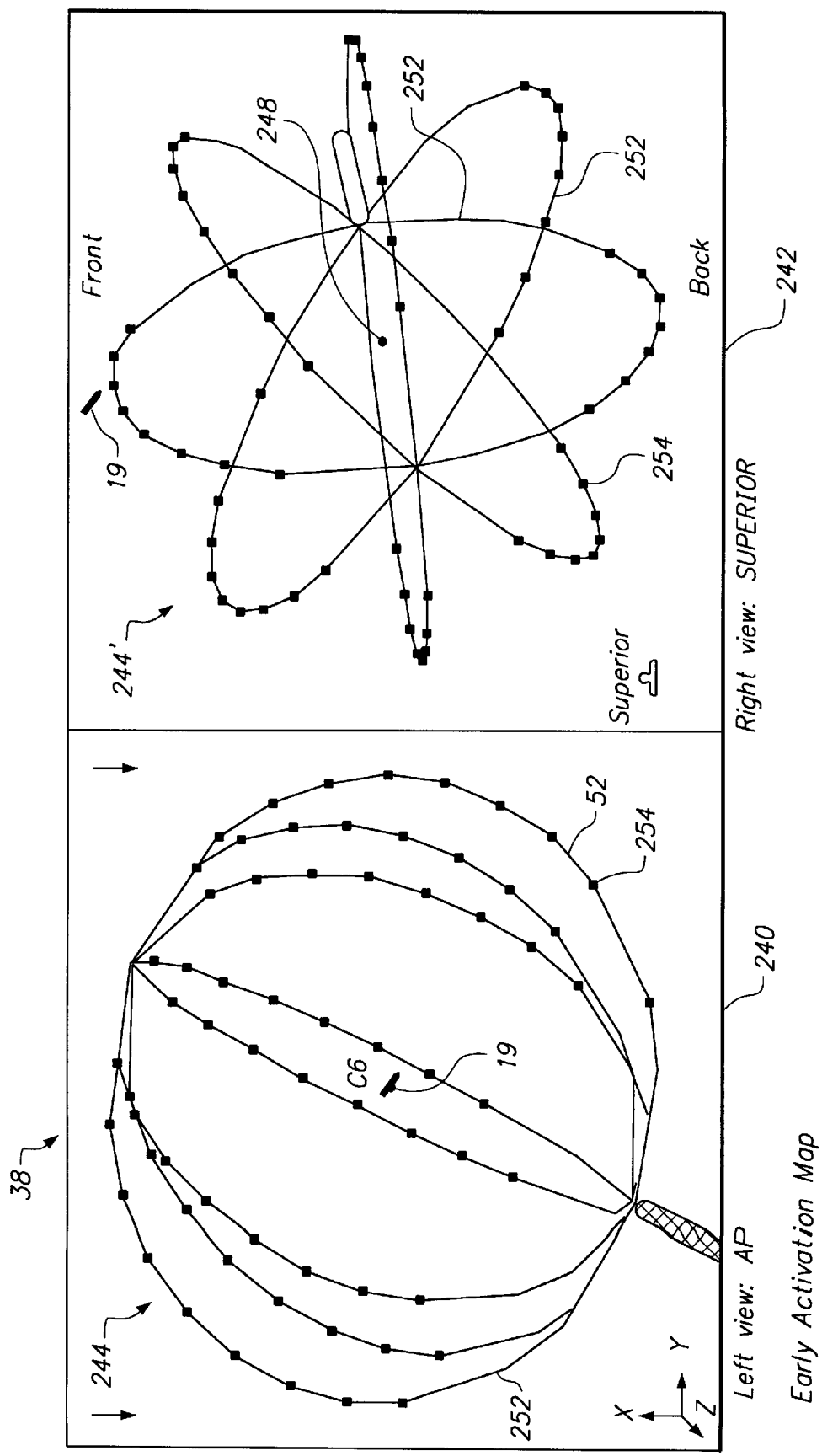
FIG. 23 is a sample of a display screen generated by the GUI showing the location of an ablation electrode during a tachycardia ablation procedure.

FIG. 23 depicts the GUI being used to guide the roving electrode 19. The view in the left panel 240 is from the AP position, while the view in the right panel 242 is from the SUPERIOR position. The relative position of the roving electrode is indicated by the elongate symbol. The highlighted symbols * adjacent the electrodes C6 and C7 indicate early activation sites. The user-entered legend indicates a potential tachycardia ablation site between these electrodes.

Figure 24:
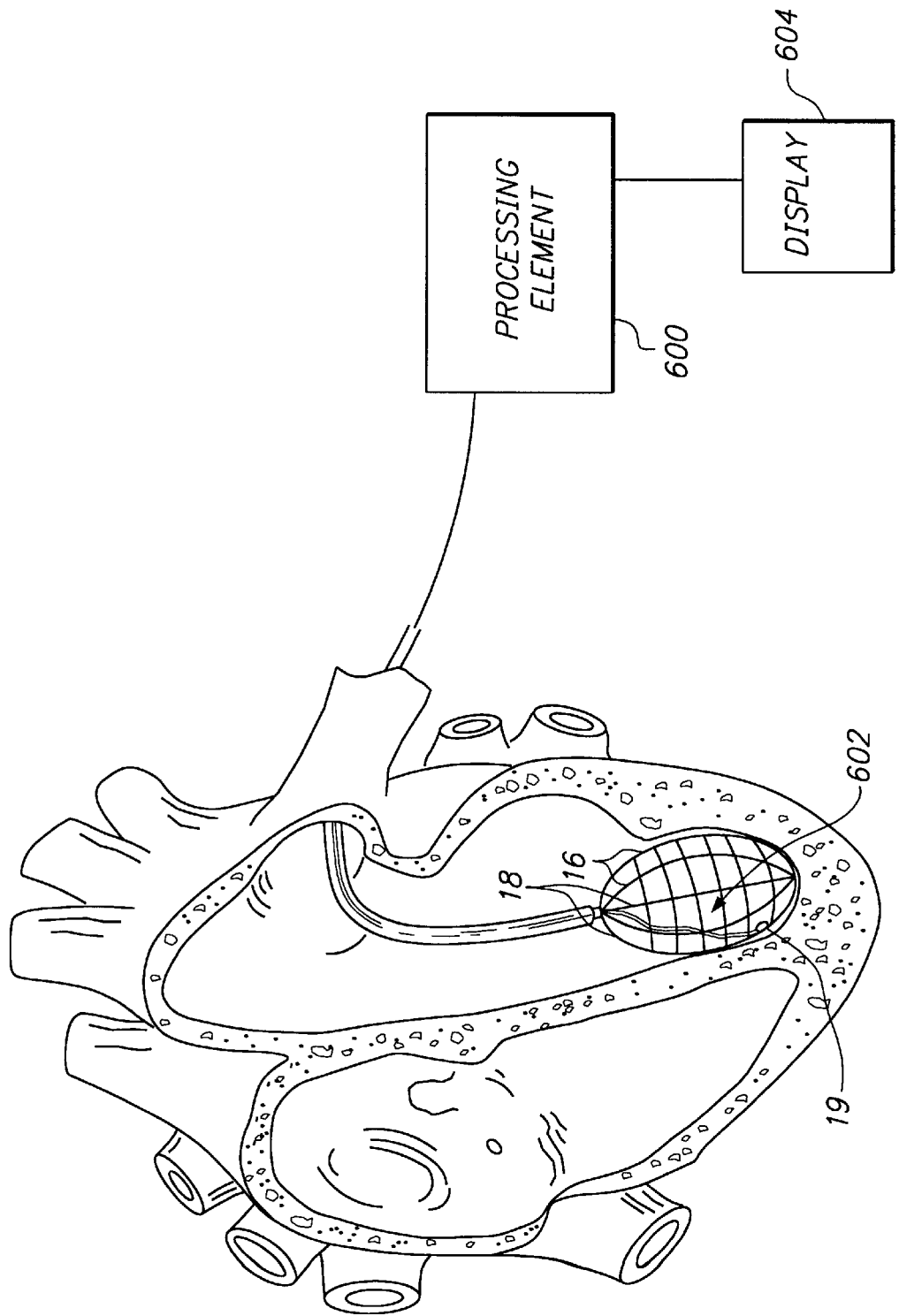
FIG. 24 is a simplified diagram useful in understanding the function and operation of a system for navigating a roving electrode within a body structure.

Preferably, the GUI provides for visualized navigation of a roving electrode or other structure within the space defined by the various electrodes. Various known navigational techniques can be used. In one arrangement shown in FIG. 24, a micro-processor controlled guidance element 600 is electrically coupled to the electrodes 16 on the splines 18 and the roving electrode 19. The element 600 conditions the electrodes 16 on the splines 18 20 and the roving electrode 19 to generate an electric field (shown in phantom lines 602 in FIG. 24) within the splines 18, while also sensing electrode electric potentials in the electric field. More particularly, the element 600 commands a transmitting electrode, which can be either the roving electrode 19 or at least one of the electrodes 16 on the splines 18, to transmit electrical energy. The element 600 commands a sensing electrode, which also can be either the roving electrode 19 or at least one of the electrodes 16 on the splines 18, to sense electrical energy emitted by the emitting electrode.

The element 600 generates an output by analyzing spatial variations in the electrical potentials within the field 602, which change based upon the relative position of the roving electrode 19 relative to electrode 16 on the splines 18. The variations can comprise variations in phase, variations in amplitude, or both. Alternatively, the element 600 generates an output by analyzing spatial variations in impedances between the transmitting and sensing electrodes. The output locates the roving electrode 19 within the space defined by the splines 18, in terms of its position relative to the position of the multiple electrodes 16 on the splines 18.

The element 600 includes an output to the GUI, which then displays (604) the position-identifying output in a real-time format most useful to the physician for remotely guiding the roving electrode 19 within the splines 18.

Further details of establishing a localized coordinate matrix within a multiple electrode structure for the purpose of locating and guiding the movable electrode within the structure are found in copending patent application Ser. No. 08/320,301, now abandoned, filed Oct. 11, 1994 and entitled "Systems and Methods for Guiding Movable Electrode Elements Within Multiple Electrode Structures." This application is incorporated herein by reference.

The GUI is preferably configured to operate on WINDOWS® compatible laptop or desktop computers. Preferably, the computer should include a 486DX or higher processor operating at a clock frequency of 66 MHZ or higher. A hard disk capacity of 360 MB, and a main memory capacity of 4 MB should be available. Preferably, the GUI is configured to run on WINDOWS® 3.1, WINDOWS 95® or NT operating systems. The GUI is preferably realized as a "C" language program created using known programming techniques.

While a particular embodiment of the invention has been shown and described, it will be obvious to those skilled in the art that changes and modifications can be made without departing from the invention in its broader aspects, and, therefore, the aim in the appended claims is to cover all such changes and modifications as fall within the true spirit and scope of the invention.

We claim:

1. A system comprising
   a structure which, in use, is deployed in an interior body region, the structure including an operative element, a switch matrix coupled to the operative element including a plurality of inputs and a plurality of outputs, a controller coupled to the switch matrix to control the switch matrix to couple the operative element to selected ones of the inputs and selected ones of the outputs in accordance with applied commands, and an interface coupled to the controller including an input element to receive operator input, a processor to generate applied commands to the controller in response to operator input, and an image controller to generate an image of the structure while coupled to the switch matrix.

2. A system according to claim 1 wherein the image controller generates markers on the image in response to signals transmitted from the operative element through the switch matrix.

3. A system according to claim 1
wherein the operative element includes an electrode.

4. A system according to claim 3
wherein the controller controls the switch matrix to condition the electrode to sense electrical events in tissue in the interior body region.

5. A system according to claim 3
wherein the controller controls the switch matrix to condition the electrode to transmit electrical energy.

6. A system according to claim 3
wherein the control circuit controls the switch matrix to condition the electrode to transmit electrical energy.

7. A system comprising
a structure which, in use, is deployed in an interior body region, the structure including an operative element, an ASIC coupled to the operative element comprising a plurality of inputs, a plurality of outputs, a cross point switch matrix including switching elements realized in a 40–100 volt BiCMOS process coupled to the inputs and to the outputs, and a control circuit coupled to the cross point switch matrix for controlling the cross point switch matrix to couple selected ones of the inputs with selected ones of the outputs in accordance with applied commands, and an interface coupled to the control circuit including an input element to receive operator input, a processor to generate applied commands to the control circuit in response to operator input, and an image controller to generate an image of the structure while coupled to the ASIC.

8. A system according to claim 7
wherein the image controller generates markers on the image in response to signals transmitted from the operative element through the ASIC.

9. A system according to claim 7
wherein the operative element includes an electrode.

10. A system according to claim 9
wherein the control circuit controls the switch matrix to condition the electrode to sense electrical events in tissue in the interior body region.

11. A system comprising
a structure which, in use, is deployed in an interior body region, the structure including a plurality of electrodes for sensing biological signals, an ASIC including a plurality of inputs operable to receive biological signals sensed by the electrodes, a plurality of outputs couplable to input channels of a biological recorder, a cross point switch matrix coupled to the inputs and to the outputs, and a control circuit coupled to the cross point switch matrix for controlling the cross point switch matrix to couple selected ones of the inputs with selected ones of the outputs in accordance with applied commands and thereby direct the biological signals sensed by selected ones of the electrodes with selected ones of the biological recorder input channels, and an interface coupled to the control circuit including an input element to receive operator input, a processor to generate applied commands to the control circuit in response to operator input, and an image controller to generate an image of the structure while coupled to the ASIC.

12. A system according to claim 11
wherein the image controller generates markers on the image in response to biological signals sensed by the electrodes.

13. A system according to claim 11 and further comprising test circuitry for detecting the existence of abnormal operating conditions.

14. A system according to claim 13 wherein the test circuitry is operable to detect open electrode conditions.

15. A system according to claim 13 wherein the test circuitry is operable to detect shorted electrode conditions.

16. A system according to claim 13 wherein the test circuitry is operable to detect shorted and open electrode conditions.

17. A system according to claim 13 wherein the test circuitry operates under the control of the control circuit.

* * * * *